United States Patent
Ritzeler et al.

(10) Patent No.: US 7,285,560 B2
(45) Date of Patent: Oct. 23, 2007

(54) INDOLE DERIVATIVES OR BENZIMIDAZOLE DERIVATIVES FOR MODULATING IκB KINASE

(75) Inventors: Olaf Ritzeler, Bad Soden (DE); Gerhard Jaehne, Frankfurt (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 321 days.

(21) Appl. No.: 10/642,970

(22) Filed: Aug. 18, 2003

(65) Prior Publication Data

US 2005/0197353 A1    Sep. 8, 2005

Related U.S. Application Data

(60) Provisional application No. 60/434,749, filed on Dec. 19, 2002.

(30) Foreign Application Priority Data

Aug. 17, 2002  (DE) ................ 102 37 722

(51) Int. Cl.
- *C07D 401/14* (2006.01)
- *C07D 403/12* (2006.01)
- *A61K 31/4184* (2006.01)
- *A61K 31/404* (2006.01)
- *C07D 239/42* (2006.01)

(52) U.S. Cl. ............ 514/275; 514/333; 514/338; 514/339; 544/296; 544/331; 546/256; 546/273.4; 546/277.4

(58) Field of Classification Search ................ 544/296, 544/331; 546/256, 273.4, 277.4; 514/275, 514/333, 338, 339
See application file for complete search history.

(56) References Cited

U.S. PATENT DOCUMENTS

| 6,358,978 | B1 | 3/2002 | Ritzeler et al. |
| 2003/0119820 | A1 | 6/2003 | Ritzeler et al. |

FOREIGN PATENT DOCUMENTS

| WO | 94/08962 | 4/1994 |
| WO | WO94/12478 | 6/1994 |

OTHER PUBLICATIONS

Douglas, Jr. Introduction to Viral Diseases, Cecil Textbook of Medicine, 20th Edition, vol. 2, pp. 1739-1747, 1996.*
Damasio, Alzheimer's Disease and Related Dementias, Cecil Textbook of Medicine, 20th Edition, vol. 2, pp. 1992-1996, 1996.*
Simone, Oncology: Introduction, Cecil Textbook of Medicine, 20th Edition, vol. 1, pp. 1004-1010, 1996.*
Layzer, Degenerative Diseases of the Nervous System, Cecil Textbook of Medicine, 20th Edition, vol. 2, pp. 2050-2057, 1996.*
Xiao et al., Retroviral oncoprotein Tax induces processing of NF-kB2/p100 in T-cells: evidence for the involvement of IKKalpha, The EMBO Journal, vol. 20, No. 23, pp. 6805-6815, 2001.*

* cited by examiner

*Primary Examiner*—Deepak Rao
(74) *Attorney, Agent, or Firm*—Julie Anne Knight; Joseph D. Rossi; Robert J. Kajubi

(57) ABSTRACT

The present invention relates to indole derivatives or benzimidazole derivatives, to processes for preparing such compounds, to pharmaceutical compositions comprising such compounds, and methods for the prophylaxis and therapy of a disease associated with an increased activity of IκB kinase comprising administering such compounds.

6 Claims, No Drawings

INDOLE DERIVATIVES OR BENZIMIDAZOLE DERIVATIVES FOR MODULATING IκB KINASE

This application claims the benefit of U.S. Provisional Application No. 60/434,749, filed Dec. 19, 2002. The content of U.S. Provisional Application 60/434,749 is incorporated herein by reference.

FIELD OF THE INVENTION

The invention relates to indole derivatives or benzimidazole derivatives which inhibit IκB kinase, to processes for preparing them and to their use as pharmaceuticals.

BACKGROUND OF THE INVENTION

Patent application WO 94/12478, the content of which is incorporated herein by reference, describes, inter alia, indole derivatives which inhibit blood platelet aggregation. Patent applications WO 01/00610 and WO 01/30774, the content of each of which is incorporated herein by reference, describe indole derivatives and benzimidazole derivatives which are able to modulate NFκB. NFκB is a heterodimeric transcription factor which is able to activate a large number of genes which encode, inter alia, proinflammatory cytokines such as IL-1, IL-2, TNFα or IL-6. NFκB is present in the cytosol of cells, where it is complexed with its naturally occurring inhibitor IκB. Stimulation of the cells, for example by cytokines, leads to the IκB being phosphorylated and subsequently broken down proteolytically. This proteolytic breakdown leads to the activation of NFκB, which then migrates into the nucleus of the cell, where it activates a large number of proinflammatory genes.

In diseases such as rheumatoid arthritis (in connection with inflammation), osteoarthritis, asthma, cardiac infarction, Alzheimer's diseases, diabetes Type II, "inflammatory bowel disease" or atherosclerosis, NFκB is activated to beyond the normal extent. The inhibition of NFκB is also of value in the treatment of cancer since it is used in such treatment on its own or to augment the cytostatic therapy. It has been demonstrated that pharmaceuticals such as glucocorticoids, salicylates or gold salts, which are used in the therapy of rheumatism, inhibit the NFκB-activating signal chain at various points or interfere directly with the transcription of the genes.

The first step in the abovementioned signal cascade is the breakdown of IκB. This phosphorylation is regulated by the specific IκB kinase. Thus far, no inhibitors are known which inhibit IκB kinase specifically.

The known inhibitors of IκB kinase frequently suffer from the disadvantage of lacking the specificity of inhibiting only one class of kinases. For example, most inhibitors of IκB kinase inhibit several different kinases at the same time because the structures of the catalytic domains of these kinases are similar. Consequently, the inhibitors act, in an undesirable manner, on many enzymes, including those which possess the vital function.

Patent application WO 01/30774, the content of which is incorporated herein by reference, has already described indole derivatives which are able to modulate NFκB and which exhibit a strong inhibitory effect on IκB kinase. However, the compounds which are disclosed in WO 01/30774, and are described in the examples, also exhibit a powerful inhibitory effect on other kinases, such as cAMP-dependent protein kinase, protein kinase C and casein kinase II. However, when their specificity is improved, some of these indole derivatives then exhibit a decrease in their ability to inhibit IκB kinase. Furthermore, the blood plasma level which can be achieved with the compounds disclosed in WO 01/30774 is insufficient for administering these derivatives orally.

In the endeavor to obtain effective compounds for treating rheumatoid arthritis (in association with inflammation), osteoarthritis, asthma, cardiac infarction, Alzheimer's diseases, cancer diseases (potentiation of treatments with cytotoxic agents) or atherosclerosis, it has now been found that the indole derivatives and benzimidazole derivatives according to the invention do not suffer from the abovementioned disadvantages. The indole derivatives and benzimidazole derivatives according to the invention are powerful inhibitors of IκB kinase, in this connection inhibiting kinases very selectively, and have a high blood plasma level following oral administration.

SUMMARY OF THE INVENTION

The invention therefore relates to the compound of formula I

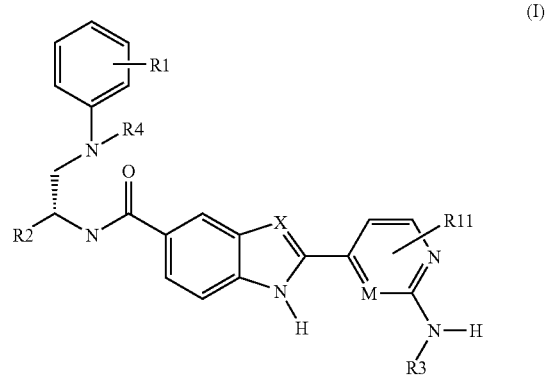

(I)

and/or a stereoisomeric form of the compound of the formula I and/or a physiologically tolerated salt of the compound of the formula I, where X and M are identical or different and are, independently of each other, N atom or CH, R1 and R11 are identical or different and are, independently of each other,
1. hydrogen atom,
2. F, Cl, I or Br,
3. —($C_1$–$C_4$)-alkyl,
4. —CN,
5. —$CF_3$,
6. —$OR^5$, in which $R^5$ is hydrogen atom or —($C_1$–$C_4$)-alkyl,
7. —N($R^5$)—$R^6$, in which $R^5$ and $R^6$ are, independently of each other, hydrogen atom or —($C_1$–$C_4$)-alkyl,
8. —C(O)—$R^5$, in which $R^5$ is hydrogen atom or —($C_1$–$C_4$)-alkyl, or
9. —S(O)$_x$—$R^5$, in which x is the integer zero, 1 or 2, and $R^5$ is hydrogen atom or —($C_1$–$C_4$)-alkyl, R2 is 1. a heteroaryl radical from the group 3-hydroxypyrro-2,4-dione, imidazole, imidazolidine, imidazoline, indazole, isothiazole, isothiazolidine, isoxazole, 2-isoxazolidine, isoxazolidine, isoxazolone, morpholine, oxazole, 1,3,4-oxadiazole, oxadiazolidinedione, oxadiazolone, 1,2,3,5-oxathiadiazole-2-oxide, 5-oxo-4,5-dihydro-[1,3,4]

oxadiazole, 5-oxo-1,2,4-thiadiazole, piperazine, pyrazine, pyrazole, pyrazoline, pyrazolidine, pyridazine, pyrimidine, tetrazole, thiadiazole, thiazole, thiomorpholine, triazole or triazolone, and the heteroaryl radical is unsubstituted or is substituted, once, twice or three times, independently of each other, by
- 1.1 —C(O)—$R^5$, in which $R^5$ is hydrogen atom or $C_1$–$C_4$-alkyl,
- 1.2 —($C_1$–$C_4$)-alkyl,
- 1.3 —O—$R^5$, in which $R^5$ is hydrogen atom or —($C_1$–$C_4$)-alkyl,
- 1.4 —N($R^5$)—$R^6$, in which $R^5$ and $R^6$ are, independently of each other, hydrogen atom or —($C_1$–$C_4$-alkyl),
- 1.5 halogen, or
- 1.6 keto radical,
2. —C(O)—$OR^5$, in which $R^5$ is hydrogen atom or —($C_1$–$C_4$-alkyl),
3. —C(O)—N($R^7$)—$R^8$, in which $R^7$ and $R^8$ are, independently of each other, hydrogen atom, —($C_1$–$C_4$)-alkyl-OH, —O—($C_1$–$C_4$)-alkyl or $C_1$–$C_4$-alkyl), R3 is hydrogen atom or —($C_1$–$C_4$-alkyl), R4 is 1. a heteroaryl radical from the group pyrrole, furan, thiophene, imidazole, pyrazole, oxazole, isoxazole, thiazole, isothiazole, tetrazole, 1,2,3,5-oxathiadiazole-2-oxides, triazolones, oxadiazolone, isoxazolone, oxadiazolidinedione, triazole, 3-hydroxypyrro-2,4-diones, 5-oxo-1,2,4-thiadiazoles, pyridine, pyrazine, pyrimidine, indole, isoindole, indazole, phthalazine, quinoline, isoquinoline, quinoxaline, quinazoline, cinnoline, β-carboline and benzofused, cyclopenta derivatives or cyclohexa derivatives of these heteroaryl radicals where the heteroaryl radical is unsubstituted or is substituted, once, twice or three times, independently of each other, by —($C_1$–$C_5$)-alkyl, —($C_1$–$C_5$)-alkoxy, halogen, nitro, amino, trifluoromethyl, hydroxyl, hydroxy-($C_1$–$C_4$)-alkyl, methylenedioxy, ethylenedioxy, formyl, acetyl, cyano, hydroxycarbonyl, aminocarbonyl or —($C_1$–$C_4$)-alkoxycarbonyl, or 2. an aryl radical from the group phenyl, naphthyl, 1-naphthyl, 2-naphthyl, biphenylyl, 2-biphenylyl, 3-biphenylyl and 4-biphenylyl, anthryl or fluorenyl, and the aryl radical is unsubstituted or is substituted, once, twice or three times, independently of each other, by —($C_1$–$C_5$)-alkyl, —($C_1$–$C_5$)-alkoxy, halogen, nitro, amino, trifluoromethyl, hydroxyl, hydroxy-($C_1$–$C_4$)-alkyl, methylenedioxy, ethylenedioxy, formyl, acetyl, cyano, hydroxycarbonyl, aminocarbonyl or —($C_1$–$C_4$)-alkoxycarbonyl.

The invention furthermore relates to compounds of the formula I, where

X and M are identical or different and are, independently of each other, N atom or CH, R1 and R11 are defined as above under 1 to 9, R2 is 1. a heteroaryl radical from the group imidazole, isothiazole, isoxazole, 2-isoxazolidine, isoxazolidine, isoxazolone, 1,3,4-oxadiazole, oxadiazolidinedione, 1,2,3,5-oxadiazolone, oxazole, 5-oxo-4,5-dihydro-[1,3,4] oxadiazole, tetrazole, thiadiazole, thiazole, triazole or triazolone, and the heteroaryl radical is unsubstituted or is substituted, once, twice or three times, independently of each other, by
- 1.1 keto radical,
- 1.2 halogen, or
- 1.3 —($C_1$–$C_2$)-alkyl, or 2. —C(O)—N($R^7$)—$R^8$, in which $R^7$ and $R^8$ are, independently of each other, hydrogen atom, —($C_1$–$C_4$)-alkyl-OH, —O—($C_1$–$C_4$)-alkyl or ($C_1$–$C_4$)-alkyl, R3 is hydrogen atom, methyl or ethyl, R4 is 1. a heteroaryl radical from the group of the unsaturated, partially saturated or completely saturated rings which are derived from pyridine, pyrazine, pyrimidine, pyridazine, pyrrole, furan, thiophene, imidazole, pyrazole, oxazole, isoxazole, thiazole, triazole or isothiazole, where the heteroaryl radical is unsubstituted or substituted, once, twice or three times, independently of each other, by —($C_1$–$C_4$)-alkyl, —($C_1$–$C_4$)-alkoxy, F, Cl, I, Br, nitro, amino, trifluoromethyl, hydroxyl, hydroxy-($C_1$–$C_4$)-alkyl, methylenedioxy, ethylenedioxy, formyl, acetyl, cyano, hydroxycarbonyl, aminocarbonyl or $C_1$–$C_4$-alkoxycarbonyl, or 2. phenyl, and phenyl is unsubstituted or is substituted, once, twice or three times, independently of each other, by F, Cl, I, Br, $CF_3$, —OH, —($C_1$–$C_4$)-alkyl or —($C_1$–$C_4$)-alkoxy.

Definition of Terms

As used above, and throughout the description of the invention, the following terms, unless otherwise indicated, shall be understood to have the following meanings.

"Patient" includes both human and other mammals.

"Pharmaceutically effective amount" is meant to describe an amount of a compound, composition, medicament or other active ingredient effective in producing the desired therapeutic effect.

"Optionally substituted" means either unsubstituted or substituted one or more times by substituents, which may be the same, or different.

The term "halogen" is understood as meaning fluorine, chlorine, bromine or iodine. The terms "—($C_1$–$C_5$)-alkyl" or "—($C_1$–$C_5$)-alkoxy" are understood as meaning hydrocarbon radicals whose carbon chain is straight-chain or branched and contains from 1 to 5 carbon atoms, such as methyl, ethyl, propyl, n-butyl, pentyl or tertiary-butyl. The expression "heteroaryl radical from the group of the unsaturated, partially saturated or completely saturated rings which are derived from pyridine, pyrazine, pyrimidine, pyridazine, pyrrole, furan, thiophene, imidazole, pyrazole, oxazole, isoxazole, thiazole and isothiazole" is understood as meaning, for example, compounds such as piperazine, pyrazoline, imidazoline, pyrazolidine, imidazolidine, tetrahydropyridine, isoxazoline, isoxazolidine, morpholine, isothiazoline, isothiazolidine, tetrahydro-1,4-thiazine or piperidine.

DETAILED DESCRIPTION OF THE INVENTION

The invention furthermore relates to the compound

N-[(S)-2-diphenylamino-1-(5-oxo-4,5-dihydro[1,3,4]oxadiazol-2-yl)ethyl]-2-(2-methylamino-pyrimidin-4-yl)-1H-indole-5-carboxamide, N-{1-carbamoyl-2-[(4-fluorophenyl)pyridin-2-ylamino] ethyl}-2-(2-methylaminopyrimidin-4-yl)-1H-indole-5-carboxamide, N-[(S)-1-(5-oxo-4,5-dihydro-1,3,4-oxadiazol-2-yl)-2-(phenylpyridin-2-ylamino)ethyl]-2-(2-methylaminopyrimidin-4-yl)-1H-indole-5-carboxamide, N-{1-carbamoyl-2-[(4-fluorophenyl)pyridin-2-ylamino] ethyl}-2-(2-aminopyrimidin-4-yl)-1H-indole-5-carboxamide, N-[2-[(4-fluorophenyl)pyridin-2-ylamino]-1-(4H-[1,2,4]
triazol-3-yl)ethyl]-2-(2-methylaminopyrimidin-4-yl)-1H-
indole-5-carboxamide, N-[1-carbamoyl-2-(phenylthiazol-2-ylamino)ethyl]-(S)-2-
(2-methylaminopyrimidin-4-yl)-H-indole-5-carboxam-
ide, N-[1-methoxycarbamoyl-2-(phenylpyridin-2-ylamino)
ethyl]-(S)-2-(2-methylaminopyrimidin-4-yl)-1H-indole-
5-carboxamide, N-{1-carbamoyl-2-[(phenyl)pyridin-2-ylamino]ethyl}-2-(2-
aminopyrimidin-4-yl)-1H-indole-5-carboxamide, N-{1-carbamoyl-2-[(phenyl)pyrimidin-2-ylamino]ethyl}-2-
(2-methylaminopyrimidin-4-yl)-1H-indole-5-carboxam-
ide, N-[1-(2-hydroxyethylcarbamoyl)-2-(phenylpyrimidin-2-
ylamino)ethyl]-2-(2-methylaminopyrimidin-4-yl)-1H-in-
dole-5-carboxamide, (S)-2-{[2-(2-methylaminopyrimidin-4-yl)-H-indole-5-car-
bonyl]amino}-3-[phenyl-(4-trifluoromethylpyrimidin-2-
yl)amino]propionic acid, N-{1-carbamoyl-2-[(4-fluorophenyl)-(5-methylpyrimidin-
2-yl)amino]ethyl}-2-(2-methylaminopyrimidin-4-yl)-1H-
indole-5-carboxamide, N-((S)-1-carbamoyl-2-diphenylaminoethyl)-2-(2-methy-
laminopyrimidin-4-yl)-1H-benzimidazole-5-carboxam-
ide, N-{1-carbamoyl-2-[(phenyl)pyrimidin-2-ylamino]ethyl}-2-
(2-methylaminopyrimidin-4-yl)-1H-benzimidazole-5-
carboxamide, or N-{1-carbamoyl-2-[(phenyl)pyridin-2-ylamino]ethyl}-2-(2-
methylaminopyrimidin-4-yl)-1H-benzimidazole-5-car-
boxamide.

The compounds of the formula I are prepared, for example, as described in patent applications WO 01/00610 and WO 01/30774, the content of each which is incorporated herein by reference.

Either the starting compounds for the chemical reactions are known or they can be readily prepared using methods known from the literature.

The invention furthermore relates to a process for preparing the compound of the formula I and/or a stereoisomeric form of the compound of the formula I and/or a physiologically tolerated salt of the compound of the formula I, which comprises a) reacting a compound of the formula IV,

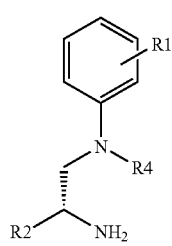

(IV)

in which R1, R2 and R4 are defined as in formula I, with an acid chloride or an activated ester of the compound of the formula III,

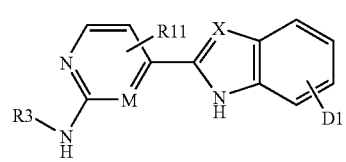

(III)

where D1 is COOH and R11, X, M and R3 are defined as in formula I, in the presence of a base or, where appropriate, of a dehydrating agent in solution, and converting the product into a compound of the formula I, b) separating a compound of the formula I, which has been prepared by method a) and which, on account of its chemical structure, appears in enantiomeric forms, into the pure enantiomers by means of forming salts with enantiomerically pure acids or bases, chromatography on chiral stationary phases or derivatization using chiral enantiomerically pure compounds such as amino acids, separating the resulting diastereomers and eliminating the chiral auxiliary groups, or c) either isolating the compound of the formula I which has been prepared by methods a) or b) in free form or, when acidic or basic groups are present, converting it into physiologically tolerated salts.

The indole carboxylic acid derivatives or benzimidazole carboxylic acid derivatives are prepared using a method described in Houben-Weyl "Methoden der Org. Chemie" [Methods of Org. Chemistry], volume E6-2A or E6-2B, the content of which is incorporated herein by reference. Thus, in order to prepare the indole carboxylic acid derivatives or benzimidazole carboxylic acid derivatives of the formula III, hydrazinobenzoic acids and aryl ketones or heteraryl ketones are preferably reacted at 145° C. in the presence of polyphosphoric acid as solvent. The necessary hydrazinobenzoic acids are prepared using methods which are familiar to the skilled person, e.g. from the corresponding benzoic acid anilines; aryl ketones or heteroaryl ketones are also prepared using methods with which the skilled person is familiar, e.g. from the corresponding acid chlorides or nitriles, by reacting them with organometallic compounds, for example.

Coupling methods of peptide chemistry which are well-known per se to the skilled person (see, e.g., Houben-Weyl, Methoden der Organischen Chemie [Methods of Organic Chemistry], volumes 15/1 and 15/2, Georg Thieme Verlag, Stuttgart, 1974, the content of which is incorporated herein by reference), are advantageously used for condensing the compounds of the formula IV with those of the formula III. Compounds such as carbonyldiimidazole, carbodiimide such as dicyclohexyl-carbodiimide or diisopropylcarbodiimide (DIC), O-((cyano(ethoxycarbonyl)methylene)-amino)-N,N,N',N'-tetramethyluronium tetrafluoroborate (TOTU) or propyl-phosphonic anhydride (PPA) are suitable for use as condensing agents or coupling reagents.

The condensations can be carried out under standard conditions. In the condensation, it is as a rule necessary for the nonreacting amino groups which are present to be protected with reversible protecting groups. The same applies to carboxyl groups which are not involved in the reaction, with these groups preferably being present, during the condensation, as —($C_1$–$C_6$)-alkyl esters, benzyl esters or tert-butyl esters. An amino group protection is not necessary if the amino groups are still present in the form of precursors such as nitro groups or cyano groups and are only formed by hydrogenation after the condensation. After the condensation, the protecting groups which are present are eliminated in a suitable manner. For example, $NO_2$ groups (guanidino protection in amino acids), benzyloxycarbonyl groups and benzyl groups in benzyl esters can be eliminated by hydrogenation. The protecting groups of the tert-butyl type are eliminated under acidic conditions while the 9-fluorenylmethyloxy-carbonyl radical is removed using secondary amines.

The invention also relates to pharmaceuticals which are characterized by an effective quantity of at least one compound of the formula I and/or a physiologically tolerated salt of the compound of the formula I and/or an optionally stereoisomeric form of the compound of the formula I, together with a pharmaceutically suitable and physiologically tolerated carrier substance, additive and/or other active compounds and auxiliary substances.

Embodiments

Because of their pharmacological properties, the compounds according to the invention are suitable for the prophylaxis and therapy of all those diseases whose course involves an increased activity of IκB kinase. These diseases include, for example, chronic diseases of the locomotory apparatus, such as inflammatory, immunologically or metabolism-mediated acute and chronic arthritides, arthropathies, rheumatoid arthritis, or degenerative joint diseases such as osteoarthroses, spondyloses, diabetes Type II, inflammatory bowel disease, loss of cartilage following joint trauma or a relatively long period of joint immobilization following meniscus or patella injuries or ligament ruptures, or diseases of the connective tissue, such as collagenoses and periodontal diseases, myalgias and disturbances of bone metabolism, or diseases which are due to overexpression of tumor necrosis factor alpha (TNFα) or an increased concentration of TNFα, such as cachexia, multiple sclerosis, craniocerebral trauma, Crohn's disease and intestinal ulcers, or diseases such as atherosclerosis, stenoses, ulceration, Alzheimer's diseases, muscle breakdown, cancer diseases (potentiation of treatment with cytotoxic agents), cardiac infarction, gout, sepsis, septic shock, endotoxic shock, viral infections such as flu, hepatitis, HIV infections, AIDS, or diseases caused by adenoviruses or herpesviruses, parasitic infections such as malaria or leprosy, fungal or yeast infections, meningites, chronic inflammatory lung diseases such as chronic bronchitis or asthma, acute respiratory distress syndrome, acute synovitis, tuberculosis, psoriasis, diabetes, treatment of acute or chronic rejection reactions on the part of the organ recipient against the transplanted organ, chronic graft-versus-host diseases and inflammatory vascular diseases. The abovementioned diseases can be treated much more specifically, and with a smaller side-effect spectrum, with the compounds which are used in accordance with the invention because it is essentially only IκB kinase which is inhibited.

The pharmaceuticals according to the invention can be administered by means of oral, inhalative, rectal or transdermal administration or by means of subcutaneous, intraarticular, intraperitoneal or intravenous injection. Oral administration is preferred.

The invention also relates to a process for producing a pharmaceutical which comprises bringing at least one compound of the formula I together with a pharmaceutically suitable and physiologically tolerated excipient and, where appropriate, other suitable active compounds, additives or auxiliary substances, into a suitable form for administration.

Examples of suitable solid or galenic preparation forms are granules, powders, sugar-coated tablets, tablets, (micro) capsules, suppositories, syrups, juices, suspensions, emulsions, drops or injectable solutions, and also preparations with protracted active compound release, in the preparation of which customary auxiliary substances, such as carrier substances, disintegrants, binders, coating agents, swelling agents, glidants or lubricants, flavorings, sweeteners and solubilizers, are used. Frequently employed auxiliary substances which may be mentioned are magnesium carbonate, titanium dioxide, lactose, mannitol and other sugars, talc, milk protein, gelatin, starch, cellulose and its derivatives, animal and vegetable oils, such as cod liver oil, sunflower oil, groundnut oil or sesame oil, polyethylene glycol and solvents, such as sterile water and monohydric or polyhydric alcohols, such as glycerol. The pharmaceutical preparations are preferably produced and administered in dosage units, with each unit containing, as the active constituent, a particular dose of the compound of the formula I according to the invention. In the case of solid dosage units, such as tablets, capsules, sugar-coated tablets or suppositories, this dose can be up to about 1 000 mg, preferably from about 50 mg to 300 mg, and, in the case of injection solutions in ampoule form, up to about 300 mg, preferably from about 10 mg to 100 mg. Depending on the activity of the compound according to the formula I, daily doses of from about 20 mg to 1 000 mg of active compound, preferably of from 100 mg to 500 mg, are indicated for treating an adult patient of about 70 kg in weight. However, higher or lower daily doses may also possibly be appropriate. The daily dose can be administered either by means of a once-only administration in the form of a single dosage unit, or of several smaller dosage units, or by means of the multiple administration of subdivided doses at predetermined intervals.

As a rule, mass-spectroscopic methods (FAB-MS, ESI-MS) are used for determining end products. Temperatures are given in degrees centigrade; RT denotes room temperature (from 22° C. to 26° C.). Abbreviations which are used are either explained or correspond to the customary conventions. The invention is explained in more detail below with the aid of examples.

EXAMPLES

Preparation Examples

A) Aniline Preparation

A.1.) 2-(p-Fluoroanilino)pyridine (3)

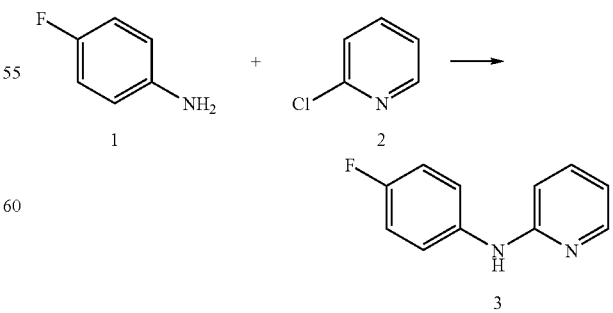

A mixture of 29.34 g (0.264 mol) of 4-fluoroaniline (1) and 29.98 g (0.264 mol) of 2-chloropyridine (2) was heated at 150° C. for 2 h. After having been cooled down to RT, it was distributed between 500 ml of 1N NaOH and 500 ml of ethyl acetate. The aqueous phase was extracted twice with in each case 300 ml of ethyl acetate and the combined organic phases were dried with magnesium sulfate. After the solvent had been evaporated, the residue was taken up in 500 ml of ethyl acetate and approx. 40 g of active charcoal were added. The mixture was stirred at RT for 10 minutes and filtered through kieselguhr. The active charcoal was rewashed 4 times with in each case 1 l of ethyl acetate. The solvent was removed in vacuo (i.v.) and the residue was precipitated from 120 ml of ethyl acetate. The solid was filtered off with suction and dried at 50° C. i.v. 41 g of 2-(p-fluoroanilino) pyridine (3) were obtained;

Yield 83%.

Empirical formula $C_{11}H_9N_2$; M.W.=188.21; MS (M+H) 189.1.

$^1$H NMR (CDCl$_3$) 6.68–6.75 (m, 2H), 6.88 (s, 1H), 7.05 (t, 2H), 7.24–7.32 (m, 2H), 7.43–7.49 (m, 1H), 8.18 (d, 1H).

A.2.) 2-(Anilino)pyrimidine (6)

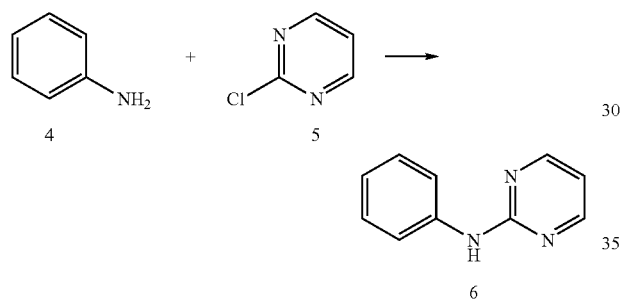

9.15 g (31%) of the anilinopyrimidine 6 were obtained from 16.2 g of aniline (4) by reaction with 2-chloropyrimidine (5) in an analogous manner to that described under A. 1.).

Empirical formula $C_{10}H_9N_3$; M.W.=171.08; MS (M+H) 172.2.

B.) Amino Acid Synthesis by Way of the Z-Serine Lactone 8

B.1.) Methyl (S)-2-amino-3-diphenylaminopropionate (11)

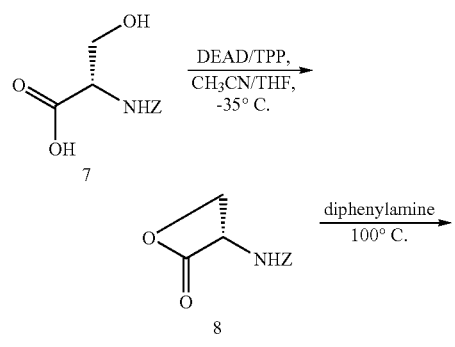

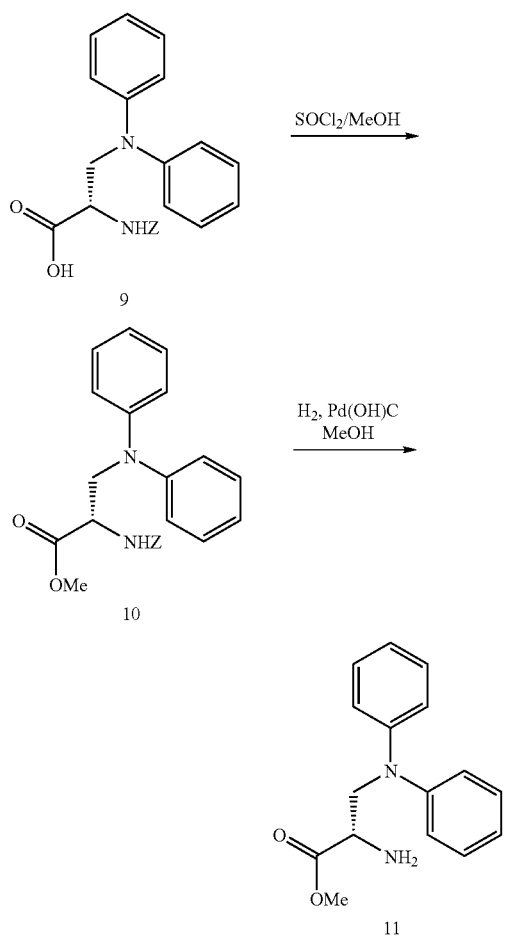

B.1.1.) N-Benzyloxycarbonyl-L-serine-β-lactone (8)

54.8 g (0.209 mol) of triphenylphosphine were suspended in 600 ml of acetonitrile, and the suspension was cooled down to from −35° C. to −45° C. while excluding moisture. 36.4 g (0.209 mol) of diethyl azodicarboxylate were added dropwise, at this temperature, within the space of 50 minutes. The mixture was then stirred at −35° C. for 15 minutes. A solution consisting of 50 g (0.209 mol) of N-benzyloxycarbonyl-L-serine (7) in 500 ml of acetonitrile was then added slowly dropwise to this mixture such that the temperature did not rise above −35° C. The resulting mixture was then stirred at 5° C. for 12 h. In order to terminate the reaction, the reaction solution was freed from the solvent under reduced pressure and the crude product was purified by medium-pressure chromatography on silica gel. (DCM/AcCN:25/1) 20.8 g of N-benzyloxycarbonyl-L-serine-β-lactone (8) were obtained after the solvent had been removed; yield 45%; (see also Org. Synth. 1991 (70) 1ff.) in fine needles.

Empirical formula $C_{11}H_{11}NO_4$; M.W.=221.2; MS (M+H) 222.1.

$^1$H NMR (DMSO-d$_6$) 4.30 (m, 1H), 4.45 (m, 1H), 5.10 (s, 2H), 5.22 (m, 2H), 7.45 (m, 5H), 8.20 (d, J=9.8 Hz, 1H).

B.1.2.) (S)-2-Benzyloxycarbonylamino-3-diphenylaminopropionic Acid (9)

5.0 g (22.6 mmol) of serine lactone (8) were stirred together with 20 g (118.2 mmol) of diphenylamine, and the mixture was heated at 100° C. for 2 h. The crude product was purified by means of medium-pressure chromatography on silica gel. (DCM/methanol: 9/1, then ethyl acetate/n-heptane: 4/1) 3.65 g (yield 42%) of clean 2-benzyloxycarbonylamino-3-diphenylaminopropionic acid (9) were obtained after the solvent had been removed.

Empirical formula $C_{23}H_{22}N_2O_4$; M.W.=390.44; MS (M+H) 391.2.

$^1$H NMR (DMSO-$d_6$) 3.85 (m, 1H), 4.18 (m, 1H), 4.3 (m, 1H), 4.9 (m, 2H), 6.9 (m, 5H), 7.25 (m, 10H).

B.1.3.) Methyl (S)-2-benzyloxycarbonylamino-3-diphenylaminopropionate (10)

6.5 ml (89.1 mmol) of thionyl chloride were added dropwise, at −5° C., to 75 ml of methanol, and the mixture was stirred for 15 min. 3.6 g (9.22 mmol) of 2-benzyloxycarbonylamino-3-diphenylaminopropionic acid (9), dissolved in 75 ml of methanol, were then added and the mixture was stirred at room temperature for a further 3 hours (h). After the solvents had been evaporated, the residue was taken up in ethyl acetate and the whole was extracted with sodium carbonate solution. Purification by means of flash chromatography (n-heptane/ethyl acetate 7:3) yielded 2.76 g (50% yield) of methyl 2-benzyloxycarbonylamino-3-diphenylaminopropionate (10).

Empirical formula $C_{24}H_{24}N_2O_4$; M.W.=404.47; MSD (M+H) 405.2.

$^1$H NMR (DMSO-$d_6$) 3.58 (s, 3H), 3.95 (m, 1H), 4.18 (m, 1H), 4.4 (m, 1H), 4.95 (m, 2H), 6.9 (m, 6H), 7.3 (m, 9H), 7.85 (d, J=9.8 Hz, 1H).

B.1.4.) Methyl (S)-2-amino-3-diphenylaminopropionate (11)

In order to eliminate the Z protecting group, 2.7 g (6.68 mmol) of the Z-protected derivative (10) were dissolved in 500 ml of methanol, and 100 mg of catalyst (10% Pd(OH)$_2$—C) were supplied under a protective atmosphere of nitrogen. The inert gas was then displaced with a large excess of hydrogen and the mixture was shaken for 2 h in the hydrogen atmosphere. In order to terminate the reaction, the catalyst was filtered off and the filtrate was concentrated. 1.65 g (yield: 91%) of methyl 2-amino-3-diphenylaminopropionate (11) were obtained.

Empirical formula $C_{16}H_{18}N_2O_2$; M.W.=270.32; MS (M+H) 271.2.

$^1$H NMR (DMSO-$d_6$) 3.45 (s, 3H), 3.58 (m, 1H), 3.8 (m, 1H), 3.95 (m, 1H), 6.9 (m, 6H), 7.3 (m, 4H).

B.2.) Amino Acid Synthesis by Way of the Acrylic Acid 13

B.2.1.) Separation of the Enantiomers

The racemic amino acids which were prepared by way of the acrylic acid were resolved into the enantiomers by means of preparative HPLC using chiral phases such as Chiralpak AD (Daicel) 100×380, RT, flow rate 300 ml/min. The purity of the enantiomers was determined by means of analytical HPLC such as Chiralpak-AD-H (Daicel) 4.6×250, 30° C., flow rate 1 ml/min, room temperature).

B.2.2. Methyl(3-(N-4-fluorophenyl-N-2-pyridyl)amino)-2-(di-tert-butyloxycarbonyl)aminopropionate (14)

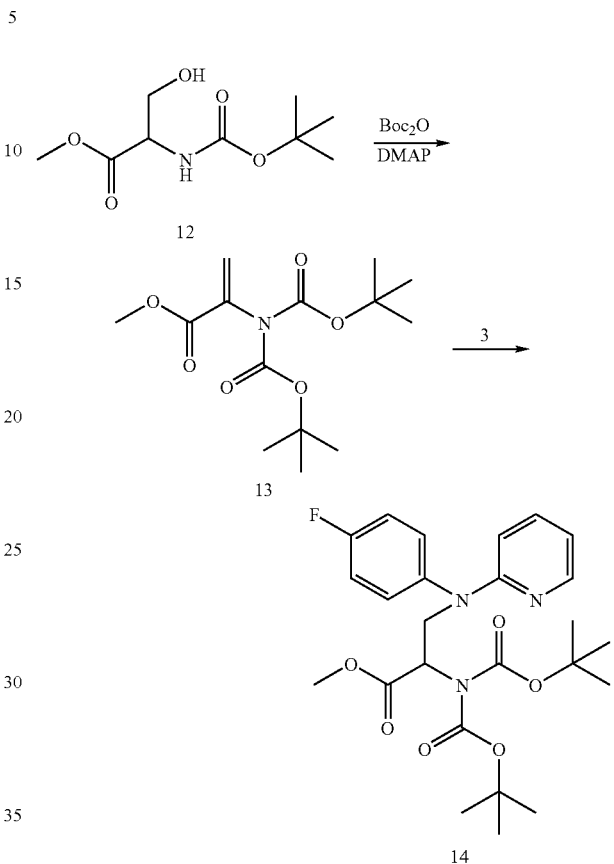

B.2.2.1.) Methyl 2-(di-tert-butyloxycarbonyl)aminoacrylate (13)

50 g (0.228 mol) of Boc-serine (12) were dissolved in 300 ml of acetonitrile. 107 g (0.493 mol) of Boc anhydride and 2.64 g (22 mmol) of DMAP were added. The mixture was stirred at RT overnight, after which the solvent was removed i.v. and the residue was taken up in 500 ml of ethyl acetate. The organic phase was washed with 500 ml of 1N HCl and dried using magnesium sulfate. 23 g of the acrylic acid 13 were obtained by crystallizing from 200 ml of heptane at −30° C. and then filtering with suction. The mother liquor was concentrated and the residue was dissolved in 140 ml of acetonitrile. 31 g (0.142 mol) of Boc anhydride and 1.26 g (10 mmol) of DMAP were added. After the mixture had been heated at 50° C. for 8 h, the solvent was removed i.v. and the residue was taken up in 500 ml of ethyl acetate. The organic phase was washed with 400 ml of 1N HCl and dried over magnesium sulfate. After the solvent had been removed i.v., a further 31.5 g of the acrylate 13 were obtained by crystallizing from heptane. Yield 54.5 g (0.181 mol) 79%.

Empirical formula $C_{14}H_{23}NO_6$;

M.W.=301.34; MS ((M*2)+Na$^+$) 625.7.

$^1$H NMR (DMSO-$d_6$) 1.40 (s, 18H), 3.74 (s, 3H), 5.85 (s, 1H), 6.28 (s, 1H).

B.2.2.2.) Methyl(3-(N-4-fluorophenyl-N-2-pyridyl)amino)-2-(di-tert-butyloxycarbonyl)aminopropionate (14)

11.5 g (38.2 mmol) of acrylate 13 were mixed with 7.2 g (38.2 mmol) of aniline 3 and 37.3 g (114 mmol) of cesium carbonate. 100 ml of acetonitrile were added and the mixture was stirred at 55° C. for 2 days. After that, it was stirred at RT for a further 2 days. The solids were filtered off with suction through kieselguhr and washed 3 times with in each case 100 ml of acetonitrile. The solvent was removed from the combined organic phases i.v. and the residue was chromatographed on silica gel using heptane/ethyl acetate 4:1. Yield: 14 g (75%) of 14.

Empirical formula $C_{25}H_{32}FN_3O_6$; M.W.=489.55; MS (M+H) 490.6.

$^1$H NMR (CDCl$_3$) 1.28 (s, 18H), 3.72 (s, 3H), 4.25 (dd, 1H), 4.75 (dd, 1H), 5.83 (dd, 1H), 6.22 (d, 1H), 6.56–6.61 (m, 1H), 7.05–7.12 (m, 2H), 7.19–7.26 (m, 3H), 8.18 (d, 1H).

B.2.3.) Methyl(3-(N-phenyl-N-2-pyrimidyl)amino)-2-(di-tert-butyloxycarbonyl)aminopropionate (15)

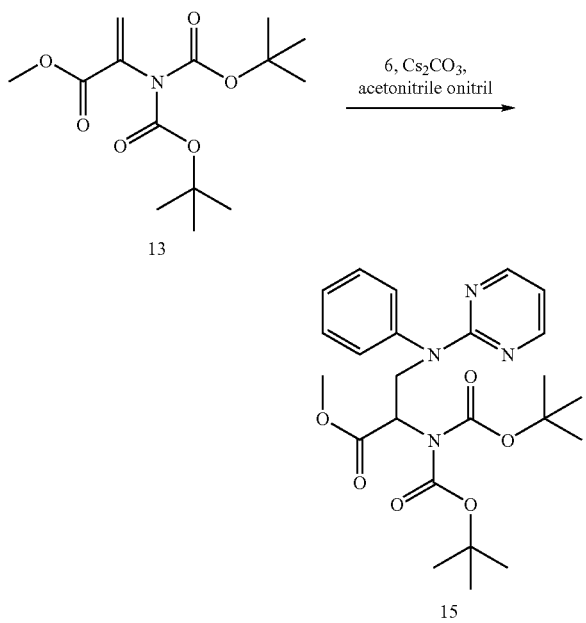

3 g (7%) of the amino acid 15 were obtained from 35 g of 6 when carrying out the reaction in an analogous manner to that described under B.2.2.2.).

Empirical formula $C_{24}H_{32}N_4O_6$; M.W.=472.23; MS (M+H) 473.1.

C.) Synthesizing the Heterocyclic Parent Substance

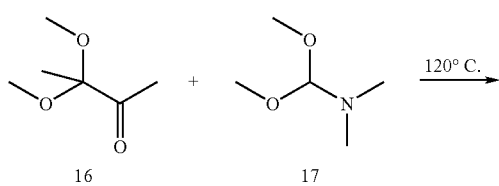

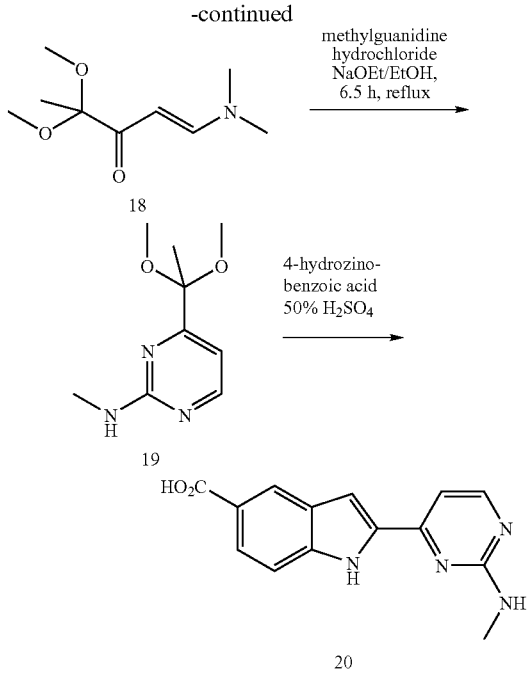

⑦ indicates text missing or illegible when filed

C.1.) Indole Parent Substance Synthesis 2-(2-Methylaminopyrimidin-4-yl)-1H-indole-5-carboxylic Acid (20)

C.1.1.) 1-Dimethylamino-4,4-dimethoxypent-1-en-3-one (18)

100 g (0.76 mol) of 3,3-dimethoxy-2-butanone (16) were stirred together with 90.2 g of N,N-dimethylformamide dimethyl acetal (17) (0.76 mol) at 120° C. for 48 h. The methanol which was formed in the reaction was removed continuously from the reaction solution by means of distillation. Crystallization occurred spontaneously when the solution was cooled, with the crystallization being brought to completion by adding a little heptane. This resulted in 128.24 g of crude product 18 (yield 90%), which was reacted without any further purification.

Empirical formula $C_9H_{17}NO_3$; M.W.=187.24; MS (M+H) 188.2.

$^1$H NMR (DMSO-d$_6$) 1.22 (s, 3H), 2.80 (s, 3H), 3.10 (s, 9H), 5.39 (d, J=15 Hz, 1H), 7.59 (d, J=15 Hz, 1H).

C.1.2.) [4-(1,1-Dimethoxyethyl)pyrimidin-2-yl]methylamine (19)

1.22 g (53 mmol) of sodium were dissolved in 100 ml of absolute ethanol. 5.8 g (53 mmol) of methylguanidine hydrochloride and 10 g (53 mmol) of 1-dimethylamino-4,4-dimethoxypent-1-en-3-one (18) were added to this solution, while stirring, and the whole was heated at boiling heat for 4 h. In order to terminate the reaction, the ethanol was evaporated. The resulting product 19 was used for the subsequent reaction without any further purification. Yield 11.5 g (58 mmol, quantitative).

Empirical formula $C_9H_{15}N_3O_2$; M.W.=197.24; MS (M+H) 198.2.

$^1$H NMR (DMSO-$d_6$) 1.45 (s, 3H), 2.78 (s, 3H), 3.10 (s, 6H), 6.75 (d, J=3 Hz, 1H), 7.0–7.1 (s(b), 1H), 8.30 (d, J=3 Hz, 1H).

C.1.3.) 2-(2-Methylaminopyrimidin-4-yl)-1H-indole-5-carboxylic Acid (20)

5 g (25 mmol) of [4-(1,1-dimethoxyethyl)pyrimidin-2-yl]methylamine (19) and 3.85 g of 4-hydrazinobenzoic acid were added, at room temperature and while stirring, to 150 ml of 50% sulfuric acid, and the mixture was heated at 130° C. for 4 h. The methanol which was formed in the reaction was removed continuously from the reaction solution by means of distillation. After it had been cooled down to 10° C., the reaction mixture was poured onto 200 ml of ice and adjusted to a pH of about 5.5 with concentrated sodium hydroxide solution. The precipitate of sodium sulfate and product mixture which was formed in the course of this was filtered off and the filter residue was extracted several times with methanol. The combined methanol extracts were concentrated and the product 20 was purified by means of flash chromatography (DCM/methanol 9:1). Yield: 0.76 g (11%).

Empirical formula $C_{14}H_{13}N_4O_2$; M.W.=268.28; MS (M+H) 269.1.

$^1$H NMR (DMSO-$d_6$) 2.95 (s, 3H), 6.90–7.10 (s(b), 1H), 7.18 (d, J=3 Hz, 1H), 7.4 (s, 1H), 7.58 (d, J=4.5 Hz, 1H), 7.80 (d, J=4.5 Hz, 1H), 8.30 (s, 1H), 7.80 (d, J=4.5 Hz, 1H), 8.38 (d, J=3 Hz, 1H), 11.85 (s, 1H), 12.40–12.60 (s(b), 1H).

C.2.) Benzimidazole Parent Substance Synthesis

2-(2-Methylaminopyrimidin-4-yl)-1H-benzimidazole-5-carboxylic Acid (25)

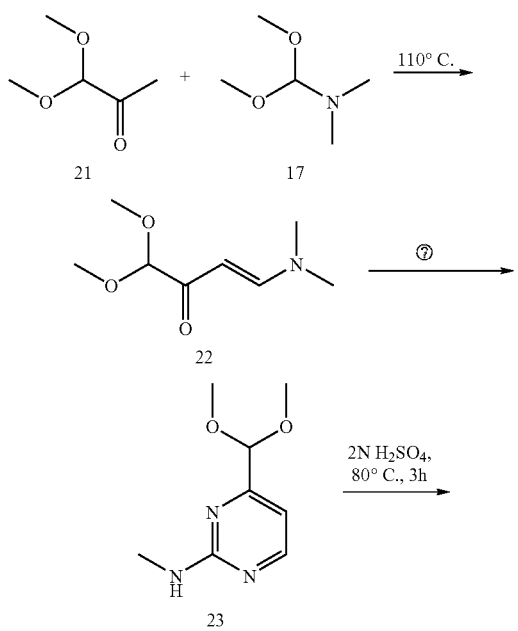

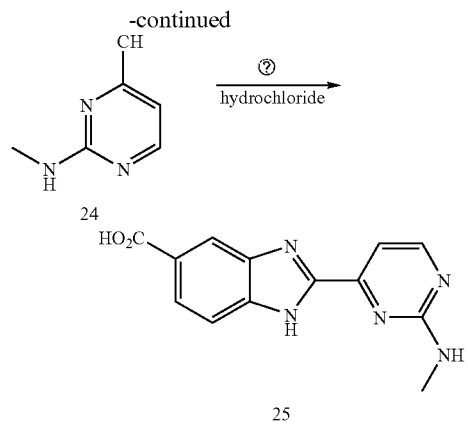

⑦ indicates text missing or illegible when filed

C.2.1.) 4-Dimethylamino-1,1-dimethoxybut-3-en-2-one (22)

300 g (307 ml, 2.54 mol) of methylglyoxal dimethyl acetal (21) were stirred, at 110° C. for 4 hours (h), together with 303 g (337 ml, 2.54 mol) of N,N-dimethylformamide dimethyl acetal (17). The methanol which was formed during the reaction was removed continuously from the reaction solution by distillation. After the reaction solution had cooled down, it was extracted with heptane and the solvent was evaporated. This resulted in 303 g of crude product 22 (yield 70%), which was reacted without any further purification.

Empirical formula $C_8H_{15}NO_3$; M.W.=173.21; MS (M+H) 174.1.

$^1$H NMR (DMSO-$d_6$) 2.10 (s, 1H), 2.80 (s, 3H), 3.10 (s, 3H), 3.25 (s, 3H), 3.3 (s, 3H), 4.42 (s, 1H), 5.19 (d (b), J=12.8 Hz, 1H), 7.60 (d, J=15 Hz, 1H).

C.2.2.) (4-Dimethoxymethylpyrimidin-2-yl)methylamine (23)

0.33 g (14.4 mmol) of sodium was dissolved in 50 ml of absolute ethanol. 1.57 g (14.4 mmol) of methylguanidine hydrochloride and 2.48 g (14.4 mmol) of 4-dimethylamino-1,1-dimethoxy-but-3-en-2-one (22) were added to this solution while stirring and the whole was heated at boiling heat for 3 h. The reaction was terminated by evaporating the ethanol. The resulting product 23 was used without any further purification. Yield 2.6 g (quantitative).

Empirical formula $C_8H_{13}N_3O_2$; M.W.=183.21; MS (M+H) 184.1. $^1$H NMR (DMSO-$d_6$) 2.78 (s, 6H), 3.10 (s, 3H), 5.02 (s, 1H), 6.62 (d, J=3 Hz, 1H), 8.30 (d, J=3 Hz, 1H).

C.2.3.) 2-Methylaminopyrimidine-4-carbaldehyde (24)

10 g (54 mmol) of (4-dimethoxymethylpyrimidin-2-yl)methylamine (23) were dissolved in 54 ml of 2N sulfuric acid and the solution was heated at 80° C. for 3 h while stirring. After the reaction had cooled, the reaction solution was carefully brought to a pH of about 9 using solid $Na_2CO_3$ and extracted 3 times with ethanol. The combined dried extracts yielded the title aldehyde 24 in 60% yield (4.47 g) after the solvent had been evaporated.

Empirical formula C$_6$H$_7$N$_3$O; M.W.=137.12; MS (M+H) 138.2.

$^1$H NMR (DMSO-d$_6$) 2.60–2.80 (s(b), 3H), 6.95 (d, J=3 Hz, 1H), 7.40–7.60 (s(b), 1H), 8.55 (d, J=3 Hz, 1H).

C.2.4.) 2-(2-Methylaminopyrimidin-4-yl)-1H-benzimidazole-5-carboxylic Acid (25)

4.3 g (31.3 mmol) of methylaminopyrimidine-4-carbaldehyde (24) and 4.8 g (31.1 mmol) of 3,4-diaminobenzoic acid were heated at 150° C. for 2 h in 300 ml of nitrobenzene. After the mixture had been cooled down to 0° C., the precipitate of the benzimidazole was separated off from the nitrobenzene by filtration and the product 25 was purified by means of flash chromatography (DCM/methanol 4:1). Yield: 2.66 g (32%).

Empirical formula C$_{13}$H$_{11}$N$_5$O$_2$; M.W.=269.28; MS (M+H) 270.2.

$^1$H NMR (DMSO-d$_6$) 2.95 (s, 3H), 7.50 (d, J=3 Hz, 1H), 7.75 (d, J=4.5 Hz, 1H), 7.90 (d, J=4.5 Hz, 1H), 8.35 (s, 1H), 8.55 (d, J=3 Hz, 1H), 8.70–9.05 (s(b), 1H).

D.) Indole End Products

D.1.) N-[(S)-2-diphenylamino-1-(5-oxo-4,5-dihydro[1,3,4]oxadiazol-2-yl)ethyl]-2-(2-methylaminopyrimidin-4-yl)-1H-indole-5-carboxamide (28)

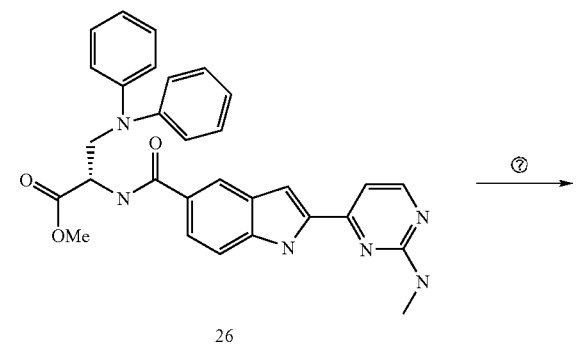

26

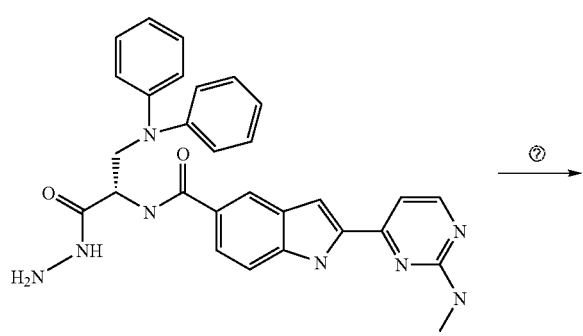

27

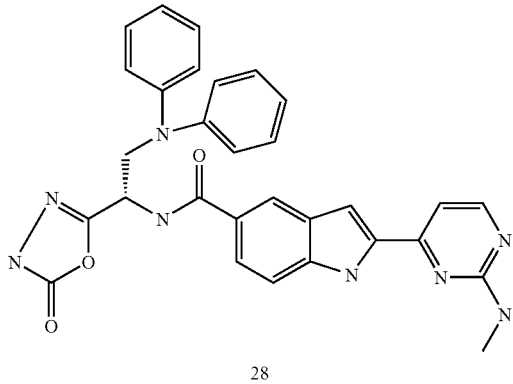

28

⑦ indicates text missing or illegible when filed

D.1.1.) Methyl 3-diphenylamino-2-{[2-(2-methylaminopyrimidin-4-yl)-1H-indole-5-carbonyl]-(S)-amino}propionate (26)

5.0 g (18.64 mmol) of 2-(2-methylaminopyrimidin-4-yl)-1H-indole-5-car-boxylic acid (20) were dissolved in 1.2 l of DMF, and 7.9 g (24.08 mmol) of TOTU and 7.9 ml (46.45 mmol) of ethyldiisopropylamine were then added consecutively. The solution was stirred at 5° C. for 20 min, after which 0.73 g (3.28 mmol) of methyl (S)-2-amino-3-diphenylaminopropionate (11) was added to it. After the mixture had been stirred for 15 h, it was concentrated under reduced pressure and the residue was taken up in n-butanol; the organic phase was then extracted with a saturated solution of sodium hydrogen carbonate in order to separate off byproducts. After the organic phase had been dried with MgSO$_4$ and concentrated, the methyl ester of the title compound 26 was isolated by flash chromatography on silica gel (DCM:MeOH=19:1). Yield: 4.3 g (98%).

Empirical formula C$_{30}$H$_{28}$N$_6$O$_3$; M.W.=520.22; MS (M+H) 521.3.

$^1$H NMR (DMSO-d$_6$) 2.95 (s(b), 3H), 3.60 (s, 3H), 4.194.58 (m, 2H), 4.85 (q, 1H), 6.90–7.10 (m, 7H), 7.18 (d, J=3 Hz, 1H), 7.25–7.40 (m, 5H), 7.50 (d, J=4.5 Hz, 1H), 7.65 (d, J=4.5 Hz, 1H), 8.05 (s, 1H), 8.35 (d, J=3 Hz, 1H), 8.70 (d, J=3.75 Hz, 1H), 11.85 (s, 1H).

D.1.2.) N-((S)-2-Diphenylamino-1-hydrazinocarbonylethyl)-2-(2-methylaminopyrimidin-4-yl)-1H-indole-5-carboxamide (27)

1.0 g (1.92 mmol) of methyl 3-diphenylamino-2-{[2-(2-methylaminopyrimidin-4-yl)-1H-indole-5-carbonyl]-(S)-amino}propionate (26) was dissolved in 10 ml of methanol, after which 0.48 g (9.95 mmol) of hydrazine hydrate was added and the mixture was stirred at RT for 15 h. The precipitate of the product (0.3 g) was separated off from the mother liquor by filtration. Further hydrazone 27 (0.1 g) was isolated from the concentrated mother liquor by means of flash chromatography on silica gel (DCM:MeOH=19:1). Yield: 0.4 g (40%).

Empirical formula C$_{29}$H$_{28}$N$_8$O$_2$; M.W.=520.6; MS (M+H) 521.4.

$^1$H NMR (DMSO-d$_6$) 2.95 (s(b), 3H), 4.02–4.58 (m, 2H), 4.4 (s, 2H), 4.85 (q, 1H), 6.90–7.10 (m, 7H), 7.18 (d, J=3 Hz,

1H), 7.20–7.45 (m, 5H), 7.50 (d, J=4.5 Hz, 1H), 7.62 (d, J=4.5 Hz, 1H), 7.99 (s, 1H), 8.25 (d, J=3 Hz, 1H), 8.35 (s(b), 1H), 9.30 (s, 1H), 11.70 (s, 1H).

D.1.3.) N-[(S)-2-Diphenylamino-1-(5-oxo-4,5-dihydro[1,3,4]oxadiazol-2-yl)ethyl]-2-(2-methylaminopyrimidin-4-yl)-1H-indole-5-carboxamide (28)

200 mg (0.384 mmol) of N-((S)-2-diphenylamino-1-hydrazinocarbonylethyl)-2-(2-methylaminopyrimidin-4-yl)-1H-indole-5-carboxamide (27) were suspended in 20 ml of methylene chloride, and a 20% solution of phosgene in toluene (0.398 mmol) was added dropwise at 0° C. and while stirring. The mixture was stirred at room temperature for a further 15 h and the solvent was evaporated. The oxadiazolone 28 was then isolated by flash chromatography on silica gel (DCM:MeOH=9:1). Yield: 160 mg (76%).

Empirical formula $C_{30}H_{26}N_8O_3$; M.W.=546.6; MS (M+H) 547.3.

$^1$H NMR (DMSO-$d_6$) 2.95 (s(b), 3H), 4.02–4.58 (m, 2H), 4.85 (q, 1H), 6.90–7.10 (m, 7H), 7.15 (d, J=3 Hz, 1H), 7.20–7.40 (m, 6H), 7.52 (d, J=4.5 Hz, 1H), 7.68 (d, J=4.5 Hz, 1H), 8.10 (s, 1H), 8.92 (d, J=3 Hz, 1H), 11.78 (s, 1H), 12.15–12.40 (s(b), 1H).

D.2.) N-{1–Carbamoyl-2-[(4-fluorophenyl)pyridin-2-ylamino]ethyl}-2-(2-methylaminopyrimidin-4-yl)-1H-indole-5-carboxylic Acid (30)

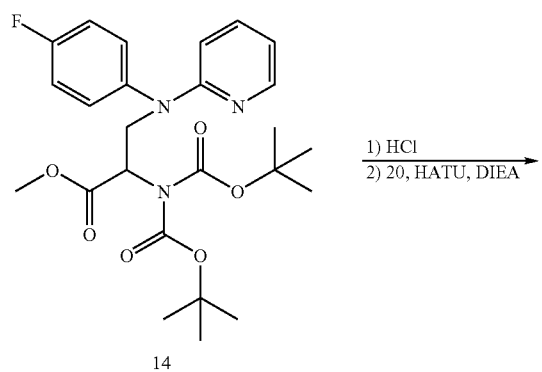

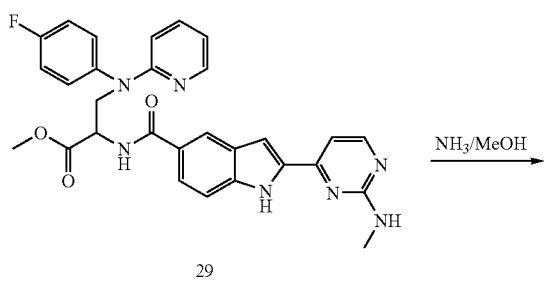

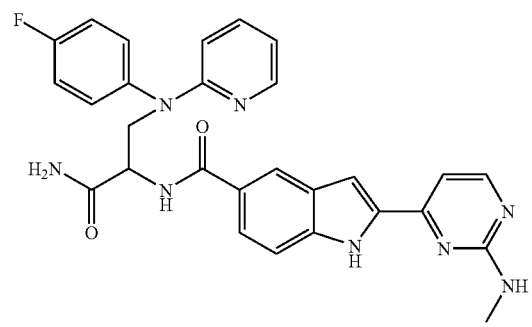

D.2.1.) Methyl 3-[(4-fluorophenyl)pyridin-2-ylamino]-2-{[2-(2-methylaminopyrimidin-4-yl)-1H-indole-5-carbonyl]amino}propionate (29)

0.75 g (1.53 mmol) of 14 was dissolved in 10 l of dioxane and the solution was cooled down to 0° C. 10 ml of 4N HCl in dioxane were added and the mixture was allowed to come to RT within the space of 2 h; It was then subsequently stirred for 12 [lacuna]. The solvent was removed i.v. The residue was taken up in 10 ml of DMF (solution A). 617 mg of the acid 20 were dissolved in 20 ml of DMF and the solution was cooled down to 0° C. 1.05 g of HATU and 1.6 ml of DIEA were added. After the mixture had been stirred at 0° C. for 40 minutes, solution A was added. The mixture was allowed to come to RT and was then subsequently stirred for 4 h. The solvent was removed i.v. and the residue was partitioned between 100 ml of a saturated (sat.) solution of NaHCO$_3$ and 100 ml of ethyl acetate. The aqueous phase was extracted 3 times with in each case 50 ml of ethyl acetate and the combined organic phases were washed with 100 ml of a saturated solution of NaCl. The organic phase was dried using magnesium sulfate. The solvents were removed i.v. and the residue was chromatographed on silica gel using heptane/ethyl acetate 1:3. 560 mg (68%) of the ester 29 were obtained.

Empirical formula $C_{29}H_{26}FN_7O_3$; M.W.=539.57; MS (M+H) 540.2.

D.2.2.) N-{1–Carbamoyl-2-[(4-fluorophenyl)pyridin-2-ylamino]ethyl}-2-(2-methylaminopyrimidin-4-yl)-1H-indole-5-carboxaminde (30).

320 mg (0.593 mmol) of the ester 29 were dissolved, at 0° C., in 50 ml of ammonia-saturated methanol. The solution was stirred for 24 h and then left to come to RT. The solvents were removed i.v. and the residue was precipitated from 5 ml of ethyl acetate. The solid was filtered off with suction and dried at 50° C. i.v. 270 mg (87%) of the amide 30 were obtained.

Empirical formula $C_{28}H_{25}FN_8O_2$; M.W.=524.56; MS (M+H) 525.2.

$^1$H NMR (DMSO-$d_6$) 2.45 (s, 3H), 4.10 (d, 1H), 4.52–4.66 (m, 2H), 6.26 (d, 1H), 6.77 (t, 1H), 7.02 (bs, 1H), 7.09–7.17 (m, 2H), 7.22–7.32 (m, 5H), 7.38–7.46 (m, 1H), 7.47–7.58 (m, 3H), 7.92 (s, 1H), 8.27–8.36 (M, 2H), 8.59 (d, 1H), 11.70 (s, 1H).

D.3.) N-[(S)-1-(5-oxo-4,5-dihydro-1,3,4-oxadiazol-2-yl)-2-(phenylpyridin-2-ylamino)ethyl]-2-(2-methylaminopyrimidin-4-yl)-1H-indole-5-carboxamide (33)

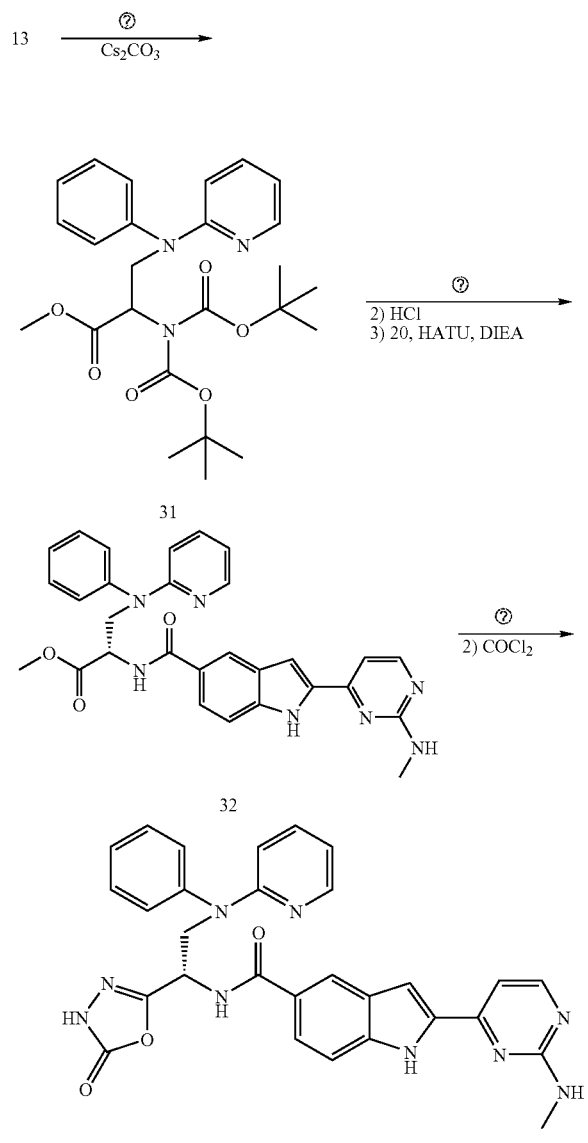

⊙ indicates text missing or illegible when filed

D.3.1.) Methyl(3-(N-phenyl-N-2-pyridyl)amino)-2-(di-tert-butyloxycarbonyl)aminopropionate (31)

4.96 g (16.5 mmol) of acrylate 13 were mixed with 5.6 g (32.9 mmol) of 2-anilinopyridine and 32.16 g (98.7 mmol) of cesium carbonate. 50 ml of acetonitrile were added and the mixture was stirred at 45° C. for 2 days. The solid was filtered off with suction through kieselguhr and washed 3 times with in each case 100 ml of acetonitrile. The combined organic phases were evaporated and the residue was chromatographed on silica gel using heptane/diethyl ether 1:1.5.66 g (73%) of the ester 31 were obtained. Empirical formula $C_{25}H_{33}N_3O_6$; M.W.=471.56; MS (M+H) 472.2.

D.3.2.) The Enantiomers were Separated as Described Under B.2.1.).

D.3.3.) Methyl 2-{[2-(2-methylaminopyrimidin-4-yl)-1H-indole-5-carbonyl]amino}-3-(phenylpyridin-2-ylamino)propionate (32)

2.9 g of the S enantiomer of 31 were dissolved in 30 ml of dioxane and the solution was cooled down to 0° C. 30 ml of 4N HCl in dioxane were added, after which the mixture was allowed to come to RT and was then stirred for 12 [lacuna]. The solvent was removed i.v. The residue was taken up in 30 ml of DMF (solution A). 2.47 g (9.2 mmol) of the acid 20 were dissolved in 50 ml of DMF and cooled down to 0° C. 4.21 g of HATU and 6.4 ml of DIEA were added. After the mixture had been stirred at 0° C. for 45 minutes, it was allowed to come to RT and solution A was added. The mixture was stirred at RT for 12 h. The solvent was removed i.v. and the residue was partitioned between 300 ml of a sat. solution of $NaHCO_3$ and 300 ml of ethyl acetate. The aqueous phase was extracted 3 times with in each case 100 ml of ethyl acetate and the combined organic phases were washed with 400 ml of a sat. solution of NaCl. The organic phase was dried with magnesium sulfate. The solvents were removed i.v. and the residue was chromatographed on silica gel using heptane/ethyl acetate 1:3. 1.78 g (55%) of the ester 32 were obtained.

Empirical formula $C_{29}H_{27}N_7O_3$; M.W.=521.58; MS (M+H) 522.2.

D.3.4.) N-[(S)-1-(5-Oxo-4,5-dihydro-1,3,4-oxadiazol-2-yl)-2-(phenylpyridin-2-ylamino)ethyl]-2-(2-methylaminopyrimidin-4-yl)-1H-indole-5-carboxamide (33)

1.78 g (3.4 mmol) of ester 32 were dissolved in 30 ml of MeOH. 0.83 ml of hydrazine hydrate was added and the mixture was stirred at 40° C. for 5 h. After that, a further 1.6 ml of hydrazine hydrate were added and the mixture was stirred at RT for 15 h. The solvents were removed i.v. and the residue was taken up in 80 ml of dichloromethane. 3.2 ml of a 20% solution of phosgene in toluene were added and the mixture was stirred for 3 days. After that, the solvent was removed i.v. and the residue was partitioned between 80 ml of water and 80 ml of ethyl acetate. When this was done, a solid precipitated out and was filtered off with suction. The organic phase was evaporated and the residue was combined with the solid and chromatographed on silica gel using heptane/ethyl acetate 1:5. 390 mg (21%) of the oxadiazolone 33 were obtained. Empirical formula $C_{29}H_{25}N_9O_3$; M.W.=547.58; MS (M+H) 548.2.

$^1$H NMR (DMSO-$d_6$) 2.96 (s, 3H), 4.30 (dd, 1H), 4.67 (dd, 1H), 5.40 (dd, 1H), 6.32 (d, 1H), 6.70–6.75 (m, 1H), 6.98 (bs, 1H), 7.16 (d, 1H), 7.22–7.33 (m, 4H), 7.38–7.46 (m, 3H), 7.52 (d, 1H), 7.63 (d, 1H), 8.08 (s, 1H), 8.21 (d, 1H), 8.31–8.35 (m, 1H), 9.00 (d, 1H), 11.72 (s, 1H), 12.15 (s, 1H).

D.4.) N-{1–Carbamoyl-2-[(4-fluorophenyl)pyridin-2-ylamino]ethyl}-2-(2-aminopyrimidin-4-yl)-1H-indole-5-carboxamide (35)

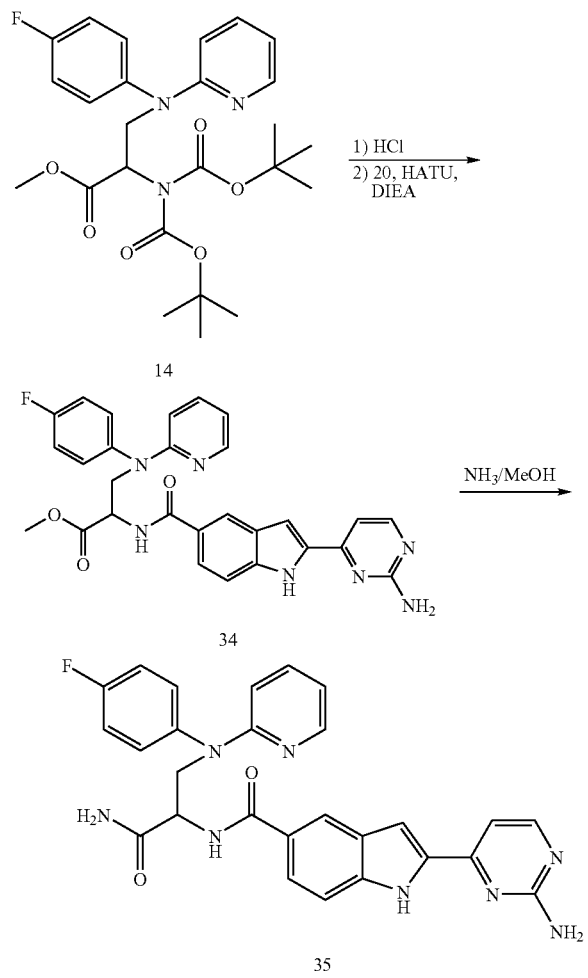

D.4.1.) Methyl 3-[(4-fluorophenyl)pyridin-2-ylamino]-2-{[2-(2-aminopyrimidin-4-yl)-1H-indole-5-carbonyl]amino}propionate (34)

370 mg (46%) of the methyl ester 34 were obtained from 750 mg of 14 when carrying out the reaction in an analogous manner to that described under D.2.1.).

Empirical formula $C_{28}H_{24}FN_7O_3$; M.W.=525.55; MS (M+H) 526.2.

D.4.2.) N-{1–Carbamoyl-2-[(4-fluorophenyl)pyridin-2-ylamino]ethyl}-2-(2-aminopyrimidin-4-yl)-1H-indole-5-carboxamide (35)

95 mg (65%) of the amide 35 were obtained from 150 mg of 34 when carrying out the reaction in an analogous manner to that described under D.2.2.).

Empirical formula $C_{27}H_{23}FN_8O_2$; M.W.=510.54; MS (M+H) 511.2.

$^1$H NMR (DMSO-$d_6$) 4.08–4.17 (m, 1H), 4.54–4.65 (m, 2H), 6.29 (d, 1H), 6.54 (s, 2H), 6.74–6.80 (m, 1H), 7.10 (s, 1H), 7.18 (d, 1H), 7.22–7.31 (m, 4H), 7.38–7.56 (m, 6H), 7.92 (s, 1H), 8.29–8.35 (m, 2H), 8.74 (d, 1H), 11.80 (s, 1H).

D.5.) N-[2-[(4-Fluorophenyl)pyridin-2-ylamino]-1-(4H-[1,2,4]triazol-3-yl)ethyl]-2-(2-methylaminopyrimidin-4-yl)-1H-indole-5-carboxamide (36)

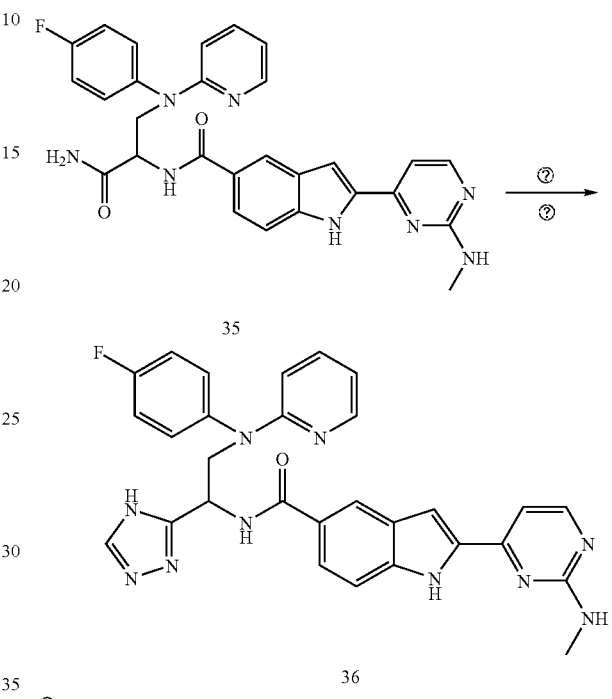

? indicates text missing or illegible when filed 130 mg (0.25 mmol) of the amide 35 were dissolved in 10 ml of DMF. 40 µl of DMF dimethyl acetal were added and the mixture was heated at 90° C. for 4 h. The solvent was removed i.v. and the residue was taken up in 3.5 ml of acetic acid. After 27 µl of hydrazine hydrate had been added, the mixture was stirred for 18 h. The solvent was removed i.v. and the residue was purified by means of preparative HPLC. 84 mg (50%) of the triazole 36 were obtained.

Empirical formula $C_{29}H_{25}FN_{10}O$; M.W.=548.59; MS (M+H) 549.2.

$^1$H NMR (DMSO-$d_6$) 3.04 (s, 3H), 4.36–4.43 (m, 1H), 4.49–4.59 (m, 1H), 5.60–5.67 (m, 1H), 6.50 (d, 1H), 6.78 (t, 1H), 7.17–7.37 (m, 7H), 7.45–7.65 (m, 4H), 8.02 (s, 1H), 8.19 (d, 1H), 8.35 (d, 1H), 8.39 (d, 1H), 11.85 (s, 1H).

D.6.) N-[1–Carbamoyl-2-(phenylthiazol-2-ylamino)ethyl]-S-2-(2-methylaminopyrimidin-4-yl)-1H-indole-5-carboxamide (42)

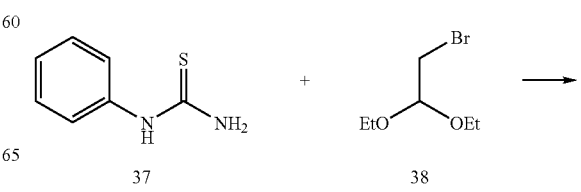

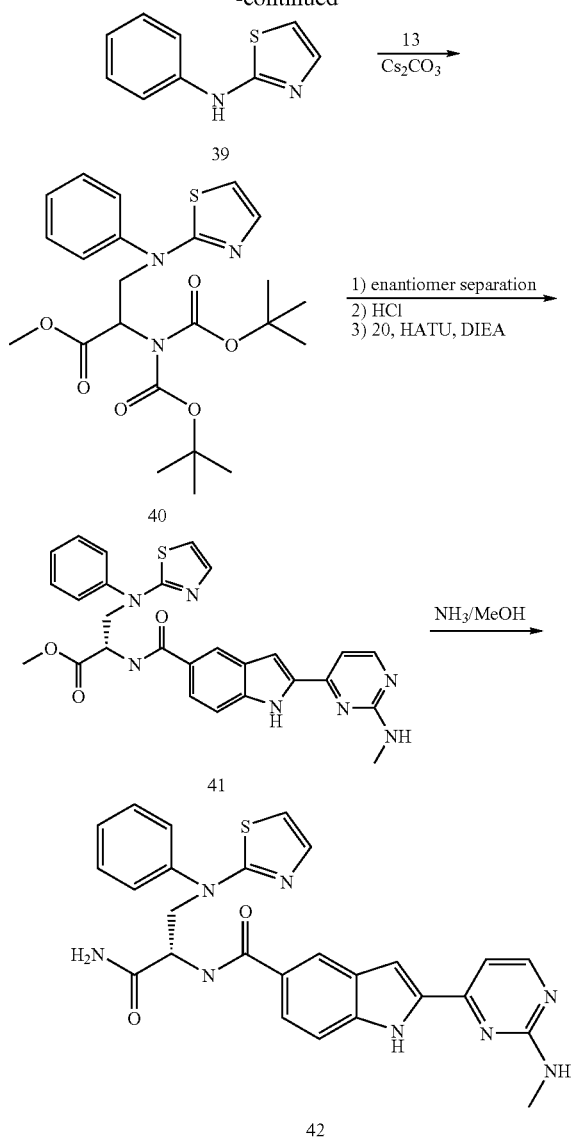

D.6.1.) Phenylthiazol-2-ylamine (39)

10 g (65.7 mmol) of phenylthiourea 37 were dissolved in 100 ml of acetic acid. 9.9 ml of the acetal 38 were added and the mixture was heated at 100° C. for 2 h. The solvent was removed i.v. and the residue was partitioned between 300 ml of 1N NaOH and 300 ml of ethyl acetate. The aqueous phase was extracted twice with in each case 100 ml of ethyl acetate and the combined organic phases were dried using magnesium sulfate. The solvent was removed and the residue was precipitated from 50 ml of diisopropyl ether. The solid was filtered off with suction and dried at 50° C. i.v. 2.5 g of aniline 39 were obtained. The diisopropyl ether mother liquor was evaporated and the residue was chromatographed on silica gel using heptane/ethyl acetate 2:1. This resulted in a further 3.5 g of 39 being obtained. Yield: 6.0 g (52%).

Empirical formula $C_9H_8N_2S$; M.W.=176.24; MS (M+H) 177.1.

D.6.2.) Methyl(3-(N-phenyl-N-2-thiazolyl)amino)-2-(di-tert-butyloxycarbonyl)amino-propionate (40)

4.5 g (75%) of the ester 40 were obtained from 3.8 g (12.5 mmol) of the acrylate 13, 2.2 g (12.5 mmol) of the aniline 39 and 20 g of cesium carbonate when carrying out the reaction in an analogous manner to that described under D.3.1.).

Empirical formula $C_{23}H_{31}N_3O_6S$; M.W.=477.58; MS (M+H) 478.2.

D.6.3.) The Enantiomers were Separated as Described Under B.2.1.).

D.6.4.) Methyl S-2-{[2-(2-methylaminopyrimidin-4-yl)-1H-indole-5-carbonyl]-amino}-3-(phenylthiazol-2-ylamino)propionate (41)

640 mg (55%) of 41 were obtained from 1.07 g (2.2 mol) of the ester 40 and 901 mg (3.3 mmol) of the acid 20 when carrying out the reaction in an analogous manner to that described under D.3.3.)

Empirical formula $C_{27}H_{25}N_7O_3S$; M.W.=527.61; MS (M+H) 528.1.

D.6.4.) N-[1–Carbamoyl-2-(phenylthiazol-2-ylamino)ethyl]-S-2-(2-methylaminopyrimidin-4-yl)-1H-indole-5-carboxamide (42)

340 mg (70%) of the amide 42 were obtained from 500 mg (0.95 mmol) of 41 when carrying out the reaction in an analogous manner to that described under D.2.2.)

Empirical formula $C_{26}H_{24}N_8O_2S$; M.W.=512.60; MS (M+H) 513.3.

$^1$H NMR (DMSO-$d_6$) 2.97 (s, 3H), 4.23–4.30 (M, 1H), 4.39–4.48 (M, 1H), 4.71–4.78 (m, 1H), 6.78 (d, 1H), 7.16 (d, 1H), 7.28–7.35 (m, 3H), 7.37–7.60 (m, 7H), 7.98 (s, 1H), 8.33 (d, 1H), 8.62 (d, 1H), 11.70 (s, 1H).

D.7.) N-[1-Methoxycarbamoyl-2-(phenylpyridin-2-ylamino)ethyl]-S-2-(2-methylaminopyrimidin-4-yl)-1H-indole-5-carboxamide (43)

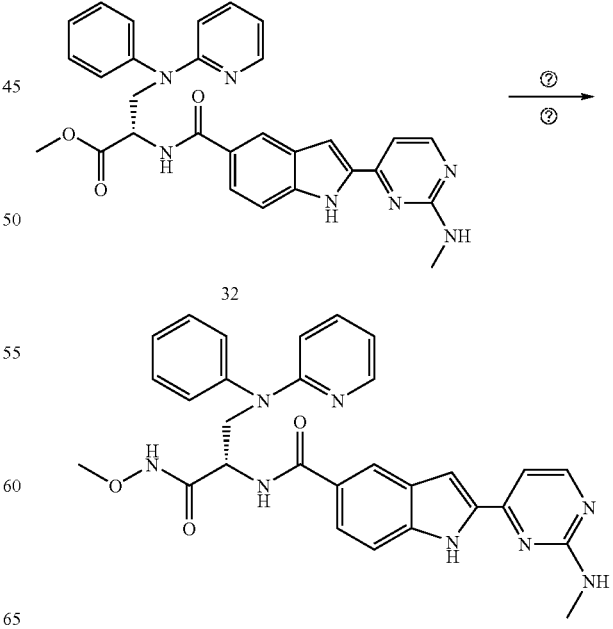

-continued 80 mg (0.95 mmol) of O-methylhydroxylamine hydrochloride were dissolved in 10 ml of THF and cooled down to −40° C. 0.95 ml (1.9 mmol) of a 2M solution of isopropyl magnesium chloride in THF was then added dropwise. The mixture was left to come to −20° C. within the space of 1 h. A solution of 100 mg (0.19 mmol) of the ester 32 in 3 ml of THF was then added dropwise. The mixture was left to come to RT within the space of 4 h and the reaction was ended by adding 5 ml of water. The THF was removed i.v. and the residue was partitioned between 20 ml of a saturated solution of ammonium chloride and 20 ml of ethyl acetate. The aqueous phase was extracted 3 times with in each case 20 ml of ethyl acetate and the combined organic phases were dried using magnesium sulfate. The solvent was removed i.v. and the residue was purified by means of preparative HPLC. 60 mg (61%) of the methyl hydroxamate 43 were obtained.

Empirical formula $C_{29}H_{28}N_8O_3$; M.W.=536.60; MS (M+H) 537.2.

$^1$H NMR (DMSO-$d_6$) 2.95 (s, 3H), 3.52 (s, 3H), 4.09–4.18 (m, 1H), 5.51–4.62 (m, 2H), 6.33 (d, 1H), 6.78 (t, 1H), 7.00 (bs, 1H), 7.18 (d, 1H), 7.25–7.33 (m, 4H), 7.49–7.61 (m, 5H), 7.98 (s, 1H), 8.29–8.36 (m, 2H), 8.79 (d, 1H), 11.31 (s, 1H), 11.75 (s, 1H).

D.8.) N-{1–Carbamoyl-2-[(phenyl)pyridin-2-ylamino]ethyl}-2-(2-aminopyrimidin-4-yl)-1H-indole-5-carboxamide (45)

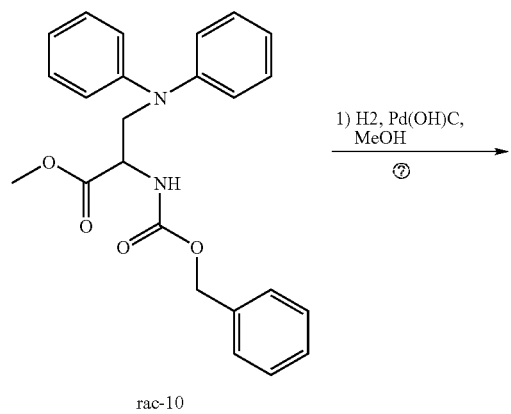

rac-10

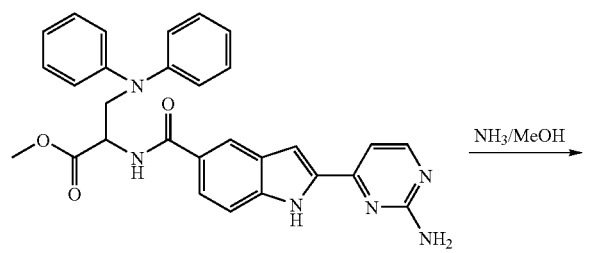

44

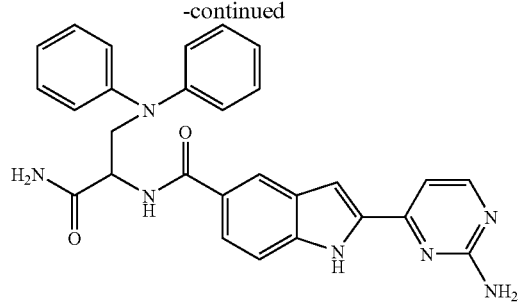

45

D.8.1.) Methyl 3-[(phenyl)pyridin-2-ylamino]-2-{[2-(2-aminopyrimidin-4-yl)-1H-indole-5-carbonyl]amino}propionate (44)

816 mg (80%) of the methyl ester 44 were obtained from 540 mg of rac-10 when carrying out the reaction in an analogous manner to that described under B.1.4.) and D.1.1.).

Empirical formula $C_{29}H_{26}N_6O_3$; M.W.=506.56; MS (M+H) 507.37.

D.8.2.) N-{1–Carbamoyl-2-[(phenyl)pyridin-2-ylamino]ethyl}-2-(2-aminopyrimidin-4-yl)-1H-indole-5-carboxamide (45)

162 mg (67%) of the amide 45 were obtained from 150 mg of 44 when carrying out the reaction in an analogous manner to that described under D.2.2.).

Empirical formula $C_{28}H_{25}N_7O_2$; M.W.=491.56; MS (M+H) 492.32. $^1$H NMR (DMSO-$d_6$) 3.18 (s(b), 3H), 4.05–4.13 (m, 2H), 4.85 (q, 1H), 6.58 (s(b), 2H), 6.88–7.59 (m, 19H), 7.98 (s, 1H), 8.25 (d, J=3 Hz, 1H), 8.35 (d, J=2 Hz, 1H), 11.78 (s, 1H).

D.9.) N-{1–Carbamoyl-2-[(phenyl)pyrimidin-2-ylamino]ethyl}-2-(2-methylaminopyrimidin-4-yl)-1H-indole-5-carboxamide (47)

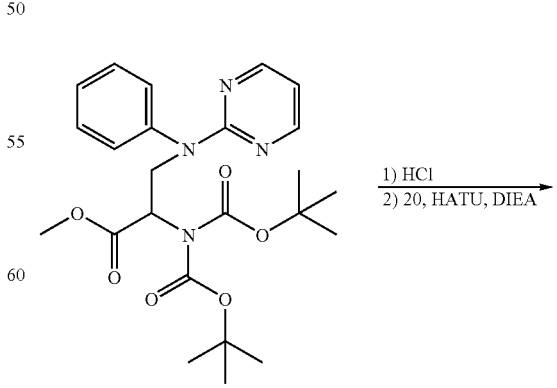

15

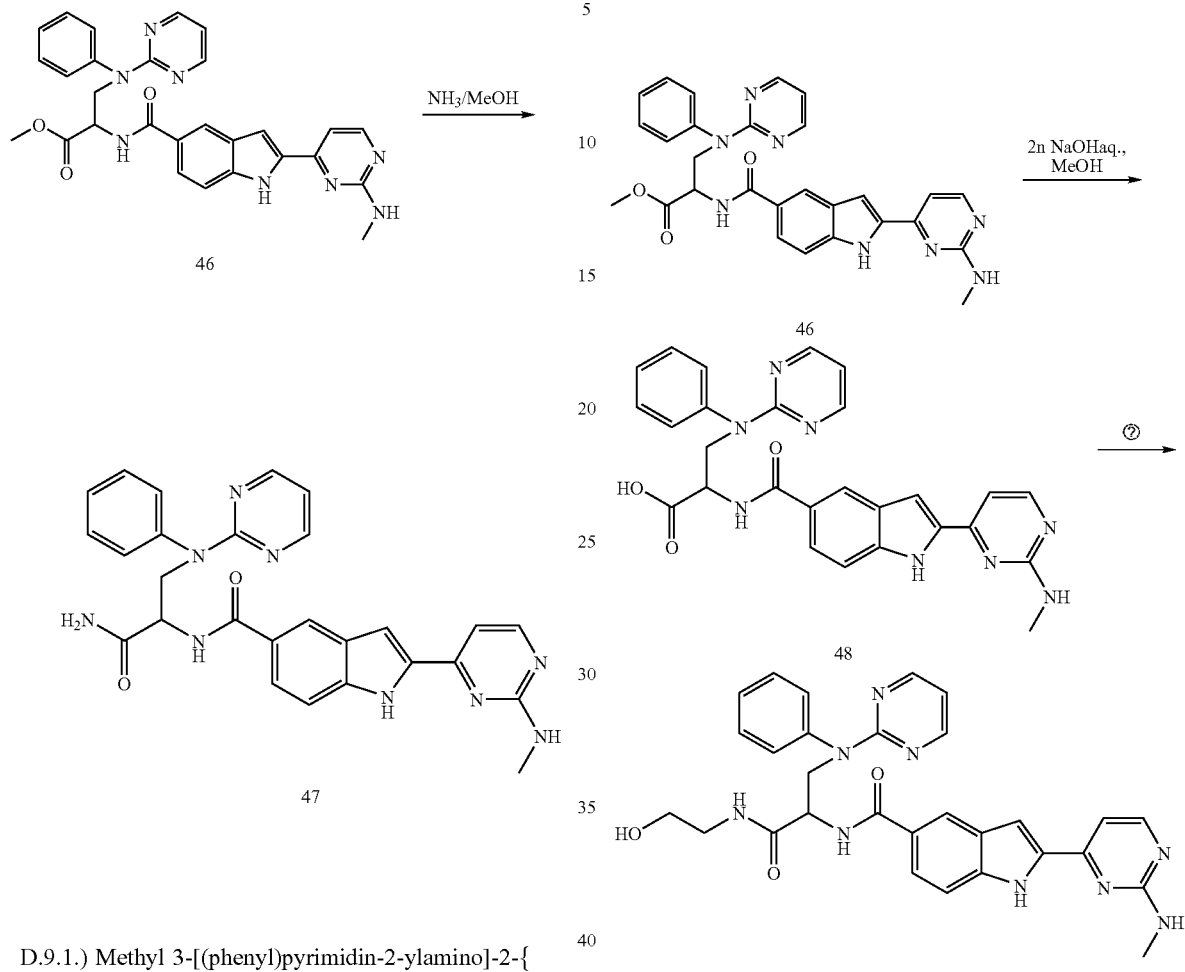

D.9.1.) Methyl 3-[(phenyl)pyrimidin-2-ylamino]-2-{[2-(2-methylamino-pyrimidin-4-yl)-1H-indole-5-carbonyl]amino}propionate (46)

1.75 mg (67%) of the methyl ester 46 were obtained from 2.36 g of 15 when carrying out the reaction in an analogous manner to that described under D.2.1.).

Empirical formula $C_{28}H_{26}N_8O_3$; M.W.=522.57; MS (1+H) 523.3.

D.9.2.) N-{1–Carbamoyl-2[(phenyl)pyrimidin-2-ylamino]ethyl}-2-(2-methylaminopyrimidin-4-yl)-1H-indole-5-carboxamide (47)

440 mg (65%) of the amide 47 were obtained from 700 mg of 46 when carrying out the reaction in an analogous manner to that described under D.2.2.).

Empirical formula $C_{27}H_{25}N_9O_2$; M.W.=507.21; MS (M+H) 508.4.

$^1$H NMR (DMSO-d$_6$) 3.0 (s(b), 3H), 4.20–4.32 (m, 1H), 4.45–4.59 (m, 2H), 4.75–4.90 (m, 1H), 6.75 (m, 1H), 7.10–7.60 (m, 12H), 7.95 (s, 1H), 8.35–8.45 (m, 4H), 11.85 (s(b), 1H).

D.10.) N-[1-(2-Hydroxyethylcarbamoyl)-2-(phenylpyrimidin-2-ylamino)ethyl]-2-(2-methylaminopyrimidin-4-yl)-1H-indole-5-carboxamide (9)

D.10.1.) 2-{[2-(2-Methylaminopyrimidin-4-yl)-1H-indole-5-carbonyl]amino}-3-(phenylpyrimidin-2-ylamino)propionic Acid (48)

4.0 g of the methyl ester 46 were dissolved in 400 ml of methanol. 40 ml of a 2N aqueous solution of NaOH were added and the whole was stirred at room temperature for 12 h. After the solvents had been evaporated, the residue was dissolved with water and the pH was adjusted to 5 using a saturated solution of NaH$_2$PO$_4$. The resulting precipitate was filtered off and washed with water. This resulted in 1.3 g (yield 93%) of the acid 48.

Empirical formula $C_{29}H_{26}N_6O_3$; M.W.=506.21; MS (M+H) 507.3.

D.10.2.) N-[1-(2-Hydroxyethylcarbamoyl)-2-(phenylpyrimidin-2-ylamino)ethyl]-2-(2-methylaminopyrimidin-4-yl)-1H-indole-5-carboxamide (49)

200 mg of the acid 48 were dissolved in 2 ml of absolute DMF. 94 mg of HOAt and 158 µl of DIEA were added. 56

μl of ethanolamine were then added dropwise and the mixture was cooled down to 0° C.; 195 mg of EDC were then added. After 2 days of stirring at room temperature, the solvent was evaporated and the crude product was purified by means of MPLC (eluent: DCM:MeOH=9:1).

Yield: 108 mg (50%) of the title amide 49.

Empirical formula $C_{31}H_{31}N_8O_2$; M.W.=549.64; MS (M+H) 550.4.

$^1$H NMR (DMSO-$d_6$) 1.2 (t, 2H), 3.0 (s(b), 3H), 3.35 (t, 1H), 4.00–4.32 (m, 2H), 4.80–4.99 (m, 1H), 6.95 (m, 1H), 7.00–7.65 (m, 7H), 7.90 (m, 1H), 8.35–8.40 (m, 1H), 11.90 (s(b), 1H).

D.11.) (S)-2-{[2-(2-Methylaminopyrimidin-4-yl)-1H-indole-5-carbonyl]amino}-3-[phenyl-(4-trifluoromethylpyrimidin-2-yl)amino]propionic Acid (54)

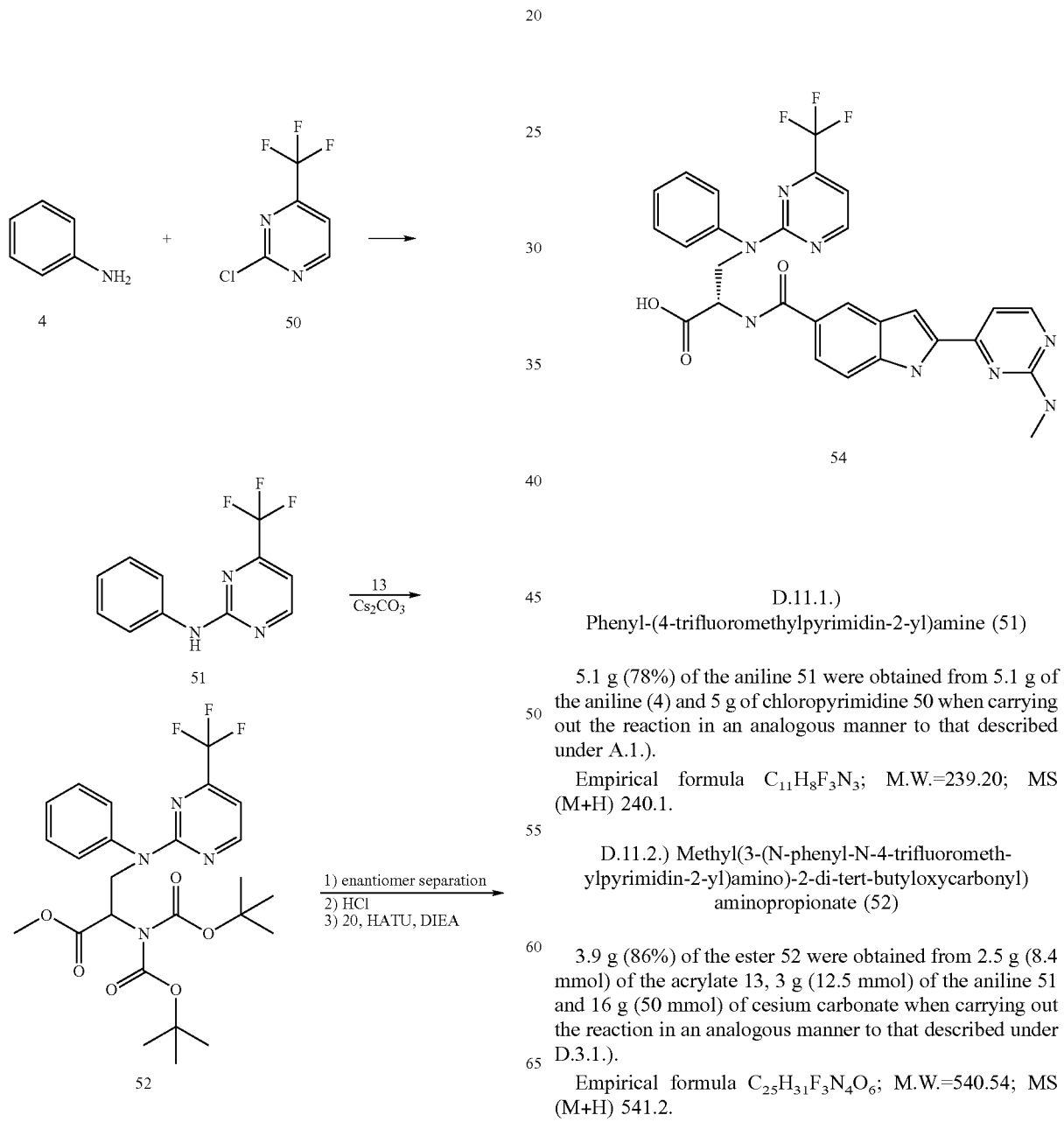

D.11.1.)
Phenyl-(4-trifluoromethylpyrimidin-2-yl)amine (51)

5.1 g (78%) of the aniline 51 were obtained from 5.1 g of the aniline (4) and 5 g of chloropyrimidine 50 when carrying out the reaction in an analogous manner to that described under A.1.).

Empirical formula $C_{11}H_8F_3N_3$; M.W.=239.20; MS (M+H) 240.1.

D.11.2.) Methyl(3-(N-phenyl-N-4-trifluoromethylpyrimidin-2-yl)amino)-2-di-tert-butyloxycarbonyl)aminopropionate (52)

3.9 g (86%) of the ester 52 were obtained from 2.5 g (8.4 mmol) of the acrylate 13, 3 g (12.5 mmol) of the aniline 51 and 16 g (50 mmol) of cesium carbonate when carrying out the reaction in an analogous manner to that described under D.3.1.).

Empirical formula $C_{25}H_{31}F_3N_4O_6$; M.W.=540.54; MS (M+H) 541.2.

D.11.3.) The Enantiomers were Separated as Described Under B.2.1.).

D.11.4.) Methyl S-2-{[2-(2-methylaminopyrimidin-4-yl)-1H-indole-5-carbonyl]amino}-3-[phenyl-(4-trifluoromethylpyrimidin-2-yl)amino]propionate (53)

467 mg (58%) of 53 were obtained from 743 mg (1.375 mmol) of the S enantiomer of the ester 52 and 550 mg (1.436 mmol) of the acid 20 when carrying out the reaction in an analogous manner to that described under D.3.3.

Empirical formula $C_{29}H_{25}F_3N_8O_3$; M.W.=590.57; MS (M+H) 591.7.

D.11.5.) (S)-2-{[2-(2-Methylaminopyrimidin-4-yl)-1H-indole-5-carbonyl]amino}-3-[phenyl-(4-trifluoromethylpyrimidin-2-yl)amino]propionic Acid (54)

38 mg (40%) of the acid 54 were obtained from 97 mg (0.164 mmol) of the ester 53 when carrying out the reaction in an analogous manner to that described under D.10.1.).

Empirical formula $C_{28}H_{23}F_3N_8O_3$; M.W.=576.54; MS (M+H) 577.7.

$^1$H NMR (DMSO-d$_6$) 2.95 (s, 3H), 4.27–4.34 (m, 1H), 4.54–4.63 (m, 1H), 4.83–4.92 (m, 1H), 6.90 (bs, 1H), 7.15 (d, 2H), 7.19–7.23 (m, 1H), 7.27–7.36 (m, 5H), 7.45–7.55 (m, 2H), 7.96 (s, 1H), 8.32 (s, 1H), 8.41 (bs, 1H), 8.66 (d, 1H), 11.70 (s, 1H).

D.12.) N-{1–Carbamoyl-2-[(4-fluorophenyl)-(5-methylpyrimidin-2-yl)amino]ethyl}-2-(2-methylaminopyrimidin-4-yl)-1H-indole-5-carboxamide (61)

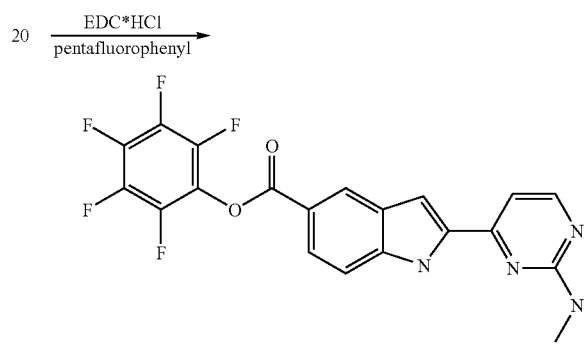

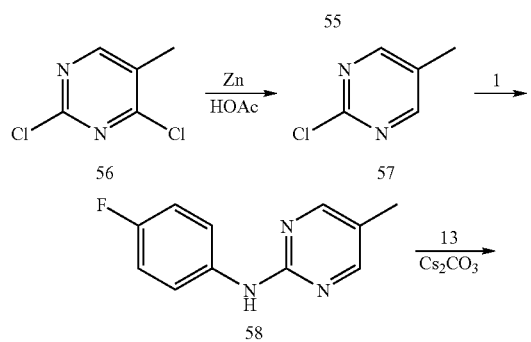

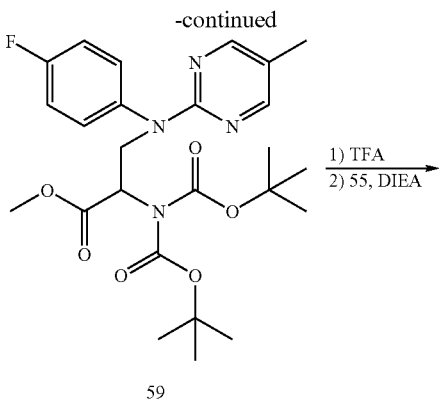

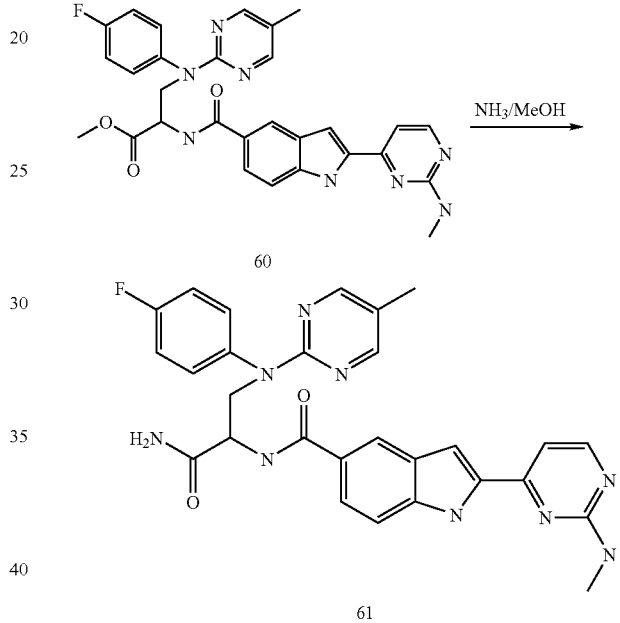

D.12.1.) Pentafluorophenyl 2-(2-methylaminopyrimidin-4-yl)-1H-indole-5-carboxylate (55)

6.38 g (23.78 mmol) of the acid 20 were suspended in 100 ml of THF. 5.25 g (28.54 mmol) of pentafluorophenol and 5.47 g (28.54 mmol) of 1-ethyl-3-(3-dimethylaminopropyl)carbodiimide hydrochloride (EDC*HCl) were then added. The mixture was stirred at RT for 15 h, after which the solvent was removed i.v. and the residue was partitioned between 300 ml of a sat. solution of NaHCO$_3$ and 300 ml of ethyl acetate. The solids were filtered off through kieselguhr and the residue was washed twice with in each 100 ml of ethyl acetate. The phases were separated and the aqueous phase was extracted twice with in each case 100 ml of ethyl acetate. The combined organic phases were washed with 200 ml of a sat. solution of NaCl and then dried with MgSO$_4$. After the solvents had been removed i.v., the residue was chromatographed on silica gel using heptane/ethyl acetate 1:1. 4.7 g (46%) of the pentafluorophenyl ester 55 were obtained.

Empirical formula $C_{20}H_{11}F_5N_4O_2$; M.W.=434.33; MS (M+H) 435.4.

D.12.2.) 2–Chloro-5-methylpyrimidine (57)

10.0 g (61.35 mmol) of 2,4-dichloro-5-methylpyrimidine (56) were dissolved in 50 ml of THF. 12.93 g (184 mmol) of zinc were added and the mixture was heated to reflux. A solution of 3.51 ml (61.35 mmol) of acetic acid in 10 ml of THF was then slowly added dropwise. After the addition had come to an end, the mixture was heated to reflux for a further 1 h. A further 1.5 ml of acetic acid in 5 ml of THF were added dropwise and the mixture was heated to reflux for 1 h. It was then left to cool down to RT, after which it was filtered through kieselguhr; this was then followed by 2 washings with in each case 20 ml of THF. The solvents were removed i.v. and the residue was chromatographed on silica gel. 4.7 g (60%) of the chloropyrimidine 57 were obtained.

Empirical formula $C_5H_5ClN_2$; M.W.=128.56; MS (M+H) 129.2.

D.12.3.) (4-Fluorophenyl)-(5-methylpyrimidin-2-yl)amine (58)

1.8 g (45%) of the aniline 58 were obtained from 2.5 g (19.45 mmol) of 2-chloro-5-methylpyrimidine (57) and 2.7 g (24.31 mmol) of 4-fluoroaniline (1) when carrying out the reaction in an analogous manner to that described under A.1.).

Empirical formula $C_{11}H_{10}FN_3$; M.W.=203.22; MS (M+H) 204.2.

D.12.4.) Methyl (3-N-4-fluorophenyl-N-5-methylpyrimidin-2-yl)amino)-2-di-tert-butyloxycarbonyl)aminopropionate (59)

2.88 g (64%) of the ester 59 were obtained from 2.67 g (8.86 mmol) of the acrylate 10, 1.8 g (8.86 mmol) of the aniline 58 and 8.66 g (26.58 mmol) of cesium carbonate when carrying out the reaction in an analogous manner to that described under D.3.1.).

Empirical formula $C_{25}H_{33}FN_4O_6$; M.W.=504.56; MS (M+H) 505.6.

D.12.5.) Methyl 3-[(4-fluorophenyl)-(5-methylpyrimidin-2-yl)amino]-2-{[2-(2-methylaminopyrimidin-4-yl)-1H-indole-5-carbonyl]amino}propionate (60)

500 mg (0.991 mmol) of the ester 59 were dissolved in 10 ml of dichloromethane and the solution was cooled down to 0° C. 5 ml of TFA were added and the mixture was then left to come to RT, after which it was stirred for 1 h. The solvents were removed i.v. The residue was taken up 10 ml of DMF, after which 430 mg (0.991 mmol) of 55 and 1.38 ml (7.93 mmol) of DIEA were added. The mixture was left to stir at RT for 15 h, after which the solvents were removed i.v. and the residue was chromatographed on silica gel using heptane/ethyl acetate 1:3. 423 mg (77%) of 60 were obtained.

Empirical formula $C_{29}H_{27}FN_8O_3$; M.W.=554.59; MS (M+H) 555.2.

D.12.6.) N-{1–Carbamoyl-2-[(4-fluorophenyl)-(5-methylpyrimidin-2-yl)amino]ethyl}-2-(2-methylaminopyrimidin-4-yl)-1H-indole-5-carboxamide (61)

250 mg (99%) of the amide 61 were obtained from 260 mg (0.469 mmol) of the ester 60 when carrying out the reaction in an analogous manner to that described under D.2.2.).

Empirical formula $C_{28}H_{26}FN_9O_2$; M.W.=539.58; MS (M+H) 540.2.

$^1$H NMR (DMSO-$d_6$) 2.11 (s, 3H), 2.95 (s, 3H), 4.21 (dd, 1H), 4.48 (dd, 1H), 4.75–4.80 (m, 1H), 7.01 (bs, 1H), 7.10–7.16 (m, 4H), 7.22–7.30 (m, 3H), 7.43 (s, 1H), 7.47–7.53 (m, 2H), 7.91 (s, 1H), 8.26 (s, 2H), 8.29.8.34 (m, 2H), 11.70 (s, 1H).

F.) Benzimidazole End Products

F.1.) N-((S)-1-carbamoyl-2-diphenylaminoethyl)-2-(2-methylaminopyrimidin-4-yl)-1H-benzoimidazole-5-carboxamide (3)

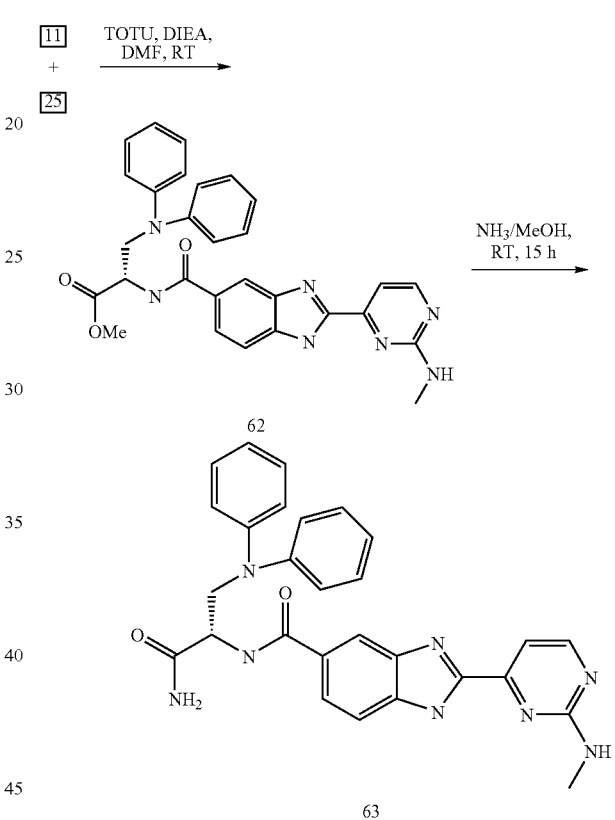

F.1.1.) Methyl 3-diphenylamino-2-{[2-(2-methylaminopyrimidin-4-yl)-1H-benzimidazole-5-carbonyl]-(S)-amino}propionate (62)

2.6 g (9.6 mmol) of 2-(2-methylaminopyrimidin-4-yl)-1H-benzimidazole-5-carboxylic acid (25) were dissolved in 300 ml of DMF, and 3.17 g (9.6 mmol) of TOTU and 1.6 ml (11.6 mmol) of ethyldiisopropylamine were added consecutively. The mixture was stirred at 5° C. for 20 min and 2.6 g (9.6 mmol) of methyl (S)-2-amino-3-diphenylaminopropionate (11) were then added to the solution. After the mixture had been stirred for 16 h, it was evaporated under reduced pressure and the methyl ester 62 was then isolated by means of flash chromatography on silica gel (DCM:MeOH=9:1).

Yield: 1.61 g (32%)

Empirical formula $C_{29}H_{27}N_7O_3$; M.W.=521.58; MS (M+H) 522.3.

¹H NMR (DMSO-d₆) 2.95 (s(b), 3H), 3.60 (s, 3H), 4.19–4.40 (m, 2H), 4.90 (q, 1H), 6.90–7.10 (m, 6H), 7.25–7.35 (m, 6H), 7.40 (d, J=4.5 Hz, 1H), 7.60–7.80 (d(b), 1H), 8.05–8.25 (d(b), 1H), 8.45 (d, J=3 Hz, 1H), 8.90 (s(b), 1H), 11.85 (s(b), 1H).

F.1.2.) N-(S)-1–Carbamoyl-2-diphenylaminoethyl)-2-(2-methylaminopyrimidin-4-yl)-1H-benzimidazole-5-carboxamide (63)

50 ml of (absolute) methanol were saturated with ammonia at 0° C. 0.5 g (0.959 mmol) of methyl 3-diphenylamino-2-{[2-(2-methylaminopyrimidin-4-yl)-1H-benzimidazole-5-carbonyl]-(S)-amino}-propionate (62) was then added and the mixture was stirred at room temperature for 24 h. After the solvent and excess ammonia had been evaporated, the amide 63 was isolated by means of flash chromatography on silica gel (DCM:MeOH=19:1). Yield: 0.43 g (89%).

Empirical formula $C_{29}H_{28}N_8O_2$; M.W.=506.57; MS (M+H) 507.2.

¹H NMR (DMSO-d₆) 2.95 (s(b), 3H), 4.02–4.35 (m, 2H), 4.85 (q, 1H), 6.80–7.10 (m, 6H), 7.15–7.25 (m, 5H), 7.40 (d, J=4.5 Hz, 1H), 7.58 (s(b), 1H), 7.68 (s(b), 1H), 8.06–8.19 (d(b), 1H), 8.40–8.58 (m, 2H), 13.10 (s, 1H).

F.2.) N-{1–Carbamoyl-2-[(phenyl)pyrimidin-2-ylamino]ethyl}-2-(2-methylaminopyrimidin-4-yl)-1H-benzimidazole-5-carboxamide (5)

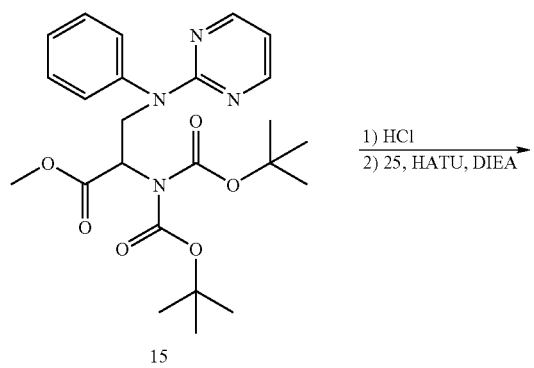

15

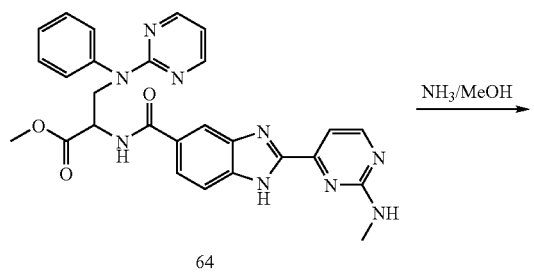

64

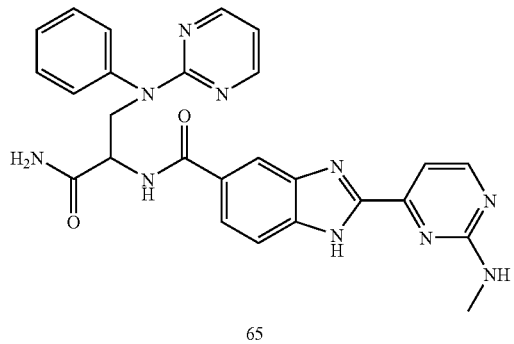

65

F.2.1.) Methyl 3-[(phenyl)pyrimidin-2-ylamino]-2-{[2-(2-methylaminopyrimidin-4-yl)-1H-benzimidazole-5-carbonyl]amino}propionate (64)

210 mg (29%) of the methyl ester 64 were obtained from 657 mg of 15 when carrying out the reaction in an analogous manner to that described under D.2.1.).

Empirical formula $C_{27}H_{25}N_9O_3$; M.W.=523.56; MS (M+H) 524.2.

F.2.2.) N-{1–Carbamoyl-2-[(phenyl)pyrimidin-2-ylamino]ethyl}2-(2-methylaminopyrimidin-4-yl)-1H-benzimidazole-5-carboxamide (65)

110 mg (65%) of the amide 65 were obtained from 200 mg of 64 when carrying out the reaction in an analogous manner to that described under D.2.2.).

Empirical formula $C_{26}H_{24}FN_{10}O_2$; M.W.=508.55; MS (M+H) 509.3.

¹H NMR (DMSO-d₆) 3.0 (s(b), 3H), 4.20–4.32 (m, 1H), 4.41–4.55 (m, 2H), 4.80–4.90 (m, 1H), 6.75 (m, 1H), 7.10–7.50 (m, 10H), 7.65 (q, 2H), 8.10 (s, 1H), 8.45 (d, 2H), 8.50 (d, 1H), 8.58 (d, 1H), 12.95 (s(b), 1H).

F.3.) N-{1–Carbamoyl-2-[(phenyl)pyridin-2-ylamino]ethyl}-2-(2-methylaminopyrimidin-4-yl)-1H-benzimidazole-5-carboxamide (67)

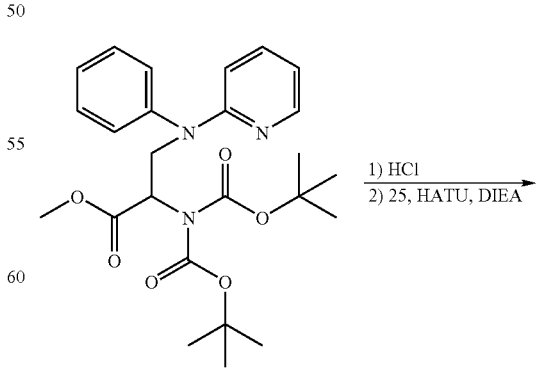

31

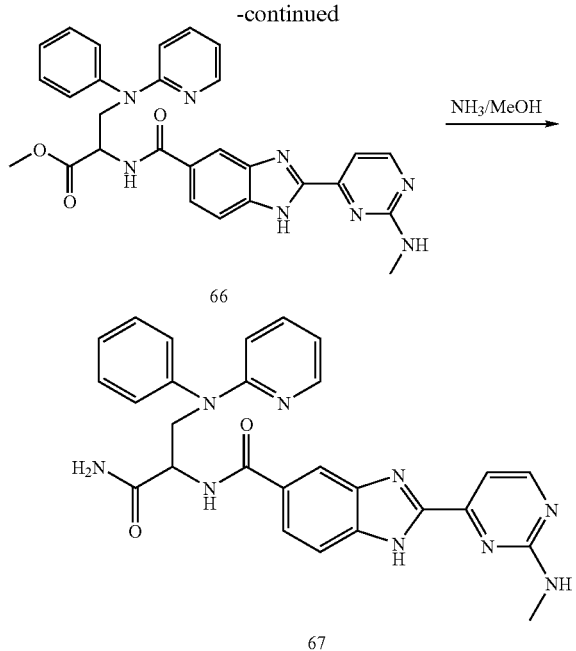

F.3.1.) Methyl 3-[(phenyl)pyridin-2-ylamino]-2-{[2-(2-methylaminopyrimidin-4-yl)-1H-benzimidazole-5-carbonyl]amino}propionate (66)

0.85 g (22%) of the methyl ester 66 was obtained from 3.44 g of 31 when carrying out the reaction in an analogous manner to that described under D.2.1.).

Empirical formula $C_{28}H_{26}N_8O_3$; M.W.=522.57; MS (M+H) 523.3.

F.3.2.) N-{1–Carbamoyl-2-[(phenyl)pyridin-2-ylamino]ethyl}-2-(2-methylaminopyrimidin-4-yl)-1H-benzimidazole-5-carboxamide (67)

160 mg (98%) of the amide 67 were obtained from 200 mg of 66 when carrying out the reaction in an analogous manner to that described under D.2.2.).

Empirical formula $C_{27}H_{25}N_9O_2$; M.W.=507.56; MS (M+HCOO⁻) 552.3.

$^1$H NMR (DMSO-d$_6$) 3.0 (s(b), 3H), 4.20–4.32 (m, 1H), 4.41–4.55 (m, 2H), 4.70–4.80 (m, 1H), 6.63 (m, 1H), 6.85 (m, 1H), 7.20–7.75 (m, 14H), 8.10 (s, 1H), 8.20 (d, 2H), 8.50 (d, 1H), 8.88 (d, 1H).

Experimental

Pharmacological Examples

IκB Kinase ELISA:

The activity of the IκB kinase was determined using an ELISA which consisted of a biotinylated substrate peptide, which contained the amino acid sequence of the IκB protein from serine 32 to serine 36, and a specific polyclonal or monoclonal antibody (e.g. obtained from New England Biolabs, Beverly, Mass., USA, cat.: 9240) which only bound to the phosphorylated form of the IκB peptide. This complex was immobilized on an antibody-binding (protein A coated) plate and detected using a conjugate composed of a biotin-binding protein and HRP (e.g. streptavidin-HRP). The activity was quantified with the aid of a standard curve which was constructed using substrate phosphopeptide.

Implementation:

In order to obtain the kinase complex, 10 ml of HeLa S3 cell extract S100 were diluted with 40 ml of 50 mM HEPES, pH 7.5, brought to 40% with respect to ammonium sulfate and incubated on ice for minutes. The precipitated pellet was dissolved in 5 ml of SEC buffer (50 mM HEPES, pH 7.5, 1 mM DTT, 0.5 mM EDTA, 10 mM 2-glycerophosphate), centrifuged at 20 000 g for 15 minutes and filtered through a 0.22 μm filter. The sample was loaded onto a 320 ml Superose-6 FPLC column (Amersham Pharmacia Biotech AB, Uppsala, Sweden) which had been equilibrated with SEC buffer and which was operated at 4° C. with a flow rate of 2 ml/min. The fractions which were located at the migration time of the 670 kDa molecular weight standard were combined for the activation. Activation was achieved by means of a 45-minute incubation with 100 nM MEKK1Δ, 250 μM MgATP, 10 mM MgCl$_2$, 5 mM dithiothreitol (DTT), 10 mM 2-glycerophosphate and 2.5 μM microcystin-LR at 37° C. The activated enzyme was stored at −80° C.

The test substances (2 μl), which were dissolved in DMSO, were preincubated, at 25° C. for 30 minutes, with 43 μl of activated enzyme (diluted 1:25 in reaction buffer 50 mM HEPES pH 7.5, 10 mM MgCl$_2$, 5 mM DTT, 10 mM β-glycerophosphate, 2.5 μM microcystin-LR). 5 μl of substrate peptide (biotin-(CH$_2$)$_6$-DRHDSGLDSMKD-CONH$_2$) (200 μM) were then added, after which the mixture was incubated for one hour and the reaction was stopped with 150 μl of 50 mM HEPES, pH 7.5, 0.1% BSA, 50 mM EDTA, antibody [1:200]. 100 μl of the stopped reaction mixture or of a standard phosphopeptide dilution series (biotin-(CH$_2$)$_6$-DRHDS[PO$_3$]GLDSMKD-CONH$_2$) were then transferred to a protein A plate (Pierce Chemical Co., Rockford, Ill., USA), after which the plate was incubated for 2 hours while being shaken. After 3 washing steps with PBS, 100 μl of 0.5 μg/ml streptavidin-HRP (horseradish peroxidase) (diluted in 50 mM HEPES/0.1% BSA) were added for 30 minutes. After 5 washing steps with PBS, 100 μL of TMB substrate (Kirkegaard & Perry Laboratories, Gaithersburg, Md., USA) were added and the color development was stopped by adding 100 μL of 0.18 M sulfuric acid. The absorption was measured at 450 nm. The standard curve was produced by linear regression corresponding to a 4-parameter dose-effect relationship. This standard curve was used to quantify the enzyme activity or its inhibition by the test substances.

The IC$_{50}$ for N-[(S)-2-diphenylamino-1-(5-oxo-4,5-dihydro[1,3,4]oxadiazol-2-yl)ethyl]-2-(2-methylaminopyrimidin-4-yl)-1H-indole-5-carboxamide was 0.050 μM.

Blood plasma level of N-[(S)-2-diphenylamino-1-(5-oxo-4,5-dihydro[1,3,4]-oxadiazol-2-yl)ethyl]-2-(2-methylaminopyrimidin-4-yl)-1H-indol-5-carboxamide.

The compound N-[(S)-2-diphenylamino-1-(5-oxo-4,5-dihydro[1,3,4]oxa-diazol-2-yl)ethyl]-2-(2-methylaminopyrimidin-4-yl)-1H-indol-5-carboxamide, termed compound 28 below, was administered to male C57/BL6 mice. For this, in each case about 25 mg of compound 28 per kg of body weight of the mice, were administered, wet-ground in 0.5% hydroxyethyl cellulose (HEC), orally as a suspension (by way of a probang). Blood samples were taken after 0.25; 0.5; 1; 2; 4; 6 and 8 hours (sacrificial blood was withdrawn from in each case 2 animals at each of the time points mentioned). The blood samples were converted into heparin plasma. The plasma samples were stored at −20° C. until analyzed.

Analysis:

The plasma samples were thawed. The plasma proteins which interfered with the analysis were then precipitated with acetonitrile.

Processing: 50 µl of plasma+20 µl of internal standard (5 µg/ml)+50 µl of buffer (2 mMol ammonium formate solution, pH 2.6/acetonitrile, 40:60, v/v) were mixed for about 10 sec on a Whirlmixer. 150 µl of acetonitrile were then added and the whole was mixed once again for about 10 sec. The samples were then centrifuged (Hettich, EBA 12, about 12 000 revolutions per minute). The supernatants (in each case about 200 µl) were transferred to glass tubes. 70 µl of the supernatant were injected.

The respective supernatant was used to determine the plasma level content of compound 13 by means of LC-MS/MS in accordance with the following method:
HPLC system: Agilent 1100
Software: Analyst
Column: 125×4 mm Nucleosil 120 5 C18 (Machery & Nagel)
Column length: 125 mm
Detection: LC-MS/MS
MS instrument: PE-Sciex API 365 (Triple Quadrupole mass spectrometer)
Software: MacQuan software (PE-Sciex)
Detection type: MS/MS (MRM)
Flow rate: 0.5 mL/min
Injection volume: 70 µl
Internal standard: SK-7 in acetonitrile
Mobile Phase: Acetonitrile/2 mMol ammonium formate solution, pH 2.6 (70:30, v/v)
Retention times (Rt):
Internal Standard: 4.4 min
Compound 28: 3.9 min The lower detection limit of the method is 0.01 µg/mL.

Results:

The plasma level of compound 28 was at most 4.3 µg/mL. The exposure, measured as AUC=area under the curve, was 5.4 µg/mL×h.

Protein Tyrosine Kinase

As examples of the specificities of the IκB kinase inhibitors which had been discovered, their $IC_{50}$ values were determined in the case of the kinase enzyme protein tyrosine kinase.

Protein tyrosine kinase activity was determined using the appropriate test kit from Upstate Biotechnologie in accordance with the manufacturer's instructions and at an ATP concentration of 50 µM. As a difference from the manufacturer's method, Multi-Screen plates (Millipore; phosphocellulose MS-PH, cat. MAPHNOB10, or Durapore PVDF, cat. MADVNOB 50), were used, together with the appropriate exhaust system, instead of phospho-cellulose filters. Poly (Glu, Tyr 4:1) (Sigma cat. P0275) was used as the test kit substrate at a test concentration of 1 mg/ml. The plates were then measured in a Wallac MicroBeta scintillation counter. 100 µM of the test substance were used in each case.

The test substance was tested in a duplicate determination. The $IC_{50}$ calculations were performed using the GraFit 3.0 software package.

The $IC_{50}$ for N-[(S)-2-diphenylamino-1-(5-oxo-4,5-dihydro[1,3,4]oxadiazol-2-yl)ethyl]-2-(2-methylaminopyrimidin-4-yl)-1H-indole-5-carboxamide (compound 28) in the protein tyrosine kinase assay was 82.5 µM.

Comparison Experiment:

The compound

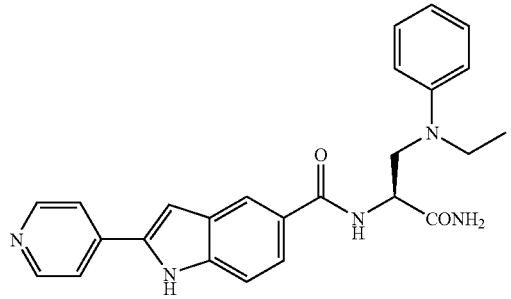

was prepared as described in WO 01/30774 and is termed the comparison compound below. The comparison compound was administered to male NMRI mice. For this, in each case about 50 mg of the comparison compound per kg of body weight of the mice were administered orally as a suspension in 0.5% HEC (by way of a probang). Blood samples were taken after 0.25; 0.5; 1; 2; 4; 6 and 8 hours (sacrificial blood was withdrawn from in each case 2 animals at each of the time points mentioned). The blood samples were converted into heparin plasma. The plasma samples were stored at −20° C. until analyzed.

Analysis: The analysis was carried out using HPLC/UV.

Processing: 50 µl of plasma+20 µl of internal standard (5 µg/ml)+50 µl of buffer (1% formic acid/acetonitrile, 40:60, v/v) were mixed for about 10 sec on a Whirlmixer. 150 µl of acetonitrile were then added and the whole was mixed once again for about 10 sec. The samples were then centrifuged (Hettich, EBA 12, about 12 000 revolutions per min). The supernatants (in each case about 200 µl) were transferred to glass tubes. 100 µl of the supernatant were injected.

The respective supernatant was used to determine the plasma level content of the comparison compound by means of HPLC/UV in accordance with the following method:
HPLC System: Gynkoteck P580 HPG pump+Gilson Abimed XL-231 Autosampler
Software: Mass-chrom
Column: 125×4 mm Protosil 120 3 ODS AQ 3 (from Bischoff)
Column length: 125 mm
Detection: LC-MS/MS
MS instrument: PE-Sciex API 365 (Triple Quadrupole mass spectrometer)
Software: MacQuan Software (PE-Sciex)
Detection type: MS/MS (MRM)
Flow rate: 0.5 mL/min
Injection volume: 100 µl
Internal Standard: SK-7 (Aventis compound) in acetonitrile
Mobile Phase: Acetonitrile/2 mMol ammonium formate solution, pH 2.6 (70:3.0, v/v)
Retention times (Rt):
Internal standard: 4 min
Comparison compound: 1.5 min At 0.01 µg/mL, the lower detection limit was identical to that when employing LC-MS/MS in the example using the compound 28.

Results: The plasma level of the comparison compound was at most 1.5 µg/mL. The exposure, measured as the AUC=area under the curve, was 1.7 µg/mL×h.

In comparison with the example using the compound 28, the maximum blood plasma level was about 60% lower in the comparison experiment even though, at 50 mg/kg, the comparison compound was administered at a dose which was twice as high as in the case of compound 28. The AUC values which were determined for the comparison compound also give the same result.

In the above-described protein tyrosine kinase assay, the $IC_{50}$ for the comparison compound was 46.35 µM. The $IC_{50}$ is therefore markedly better than in the case of compound 28. The improvement in the specificity with regard to the IκB kinase becomes even clearer when the ratios of the $IC_{50}$ values for protein tyrosine kinase relative to IκB kinase are compared. In the case of compound 28, this ratio is 1650 (82.5/0.05) while in the case of the comparison compound it is 46.35 (46.35/1.0; in accordance with the data from WO 01/30774).

The specificity ratios and/or plasma levels and exposure of the other examples were determined in an analogous manner.

| Example No. | Molecular formula neutral compound | Molecular weight | IKK IC50 50 µM | Specificity ratio |
|---|---|---|---|---|
| 28 | C30H26N8O3 | 546.59 | 0.05 | 1650 |
| 30 | C28H25FN8O2 | 524.56 | 0.05 | >200 |
| 33 | C29H25N9O3 | 547.58 | 0.012 | >833 |
| 35 | C27H23FN8O2 | 510.54 | 0.01 | >1000 |
| 36 | C29H25FN10O | 548.59 | 0.005 | >2000 |
| 42 | C26H24N8O2S | 512.60 | 0.009 | >1110 |
| 43 | C29H28N8O3 | 536.60 | 0.0008 | >12500 |
| 45 | C28H25N7O2 | 491.55 | 0.015 | >665 |
| 47 | C27H25N9O2 | 507.56 | 0.006 | >1665 |
| 49 | C31H31N7O3 | 549.63 | 0.035 | >285 |
| 54 | C28H23F3N8O3 | 576.54 | 0.003 | >3330 |
| 61 | C28H26FN9O2 | 539.58 | 0.006 | >1650 |
| 63 | C28H26N8O2 | 506.57 | 0.003 | >1000 |
| 65 | C26H24N10O2 | 508.55 | 0.004 | >2500 |
| 67 | C27H25N9O2 | 507.56 | 0.002 | >5000 |

>denotes better than

We claim:

1. A compound of the formula I,

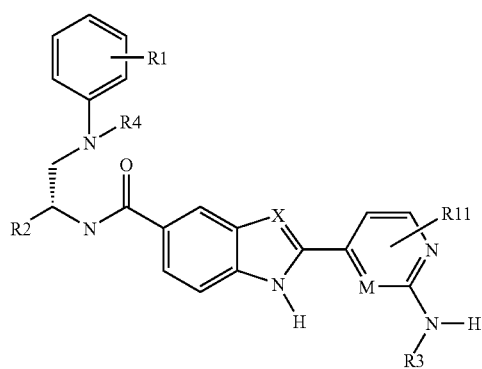

(I)

wherein:
X is N or CH;
M is N or CH;
R1 is hydrogen,
   halogen chosen from F, Cl, I and Br,
   —$(C_1–C_4)$-alkyl,
   —CN,
   —$CF_3$,
   —$OR^5$, wherein $R^5$ is hydrogen or —$(C_1–C_4)$-alkyl,
   —$N(R^5)$—$R^6$, wherein $R^5$ and $R^6$ are selected independently from hydrogen and —$(C_1–C_4)$-alkyl,
   —$C(O)$—$R^5$, wherein $R^5$ is hydrogen or —$(C_1–C_4)$-alkyl, or
   —$S(O)_x$—$R^5$, wherein x is the integer zero, 1 or 2, and wherein $R^5$ is hydrogen or —$(C_1–C_4)$-alkyl;
R2 is a heteroaryl radical, which is selected from 3-hydroxypyrro-2,4-dione, imidazole, imidazolidine, imidazoline, indazole, isothiazole, isothiazolidine, isoxazole, 2-isoxazolidine, isoxazolidine, isoxazolone, morpholine, oxazole, 1,3,4-oxadiazole, oxadiazolidinedione, oxadiazolone, 1,2,3,5-oxathiadiazole-2-oxide, 5-oxo-4,5-dihydro[1,3,4]oxadiazole, 5-oxo-1,2,4-thiadiazole, piperazine, pyrazine, pyrazole, pyrazoline, pyrazolidine, pyridazine, pyrimidine, tetrazole, thiadiazole, thiazole, thiomorpholine, triazole and triazolone, wherein the heteroaryl radical is optionally substituted one, two, or three times by
   —$C(O)$—$R^5$, wherein $R^5$ is selected from hydrogen and —$(C_1–C_4)$-alkyl,
   —$(C_1–C_4)$-alkyl,
   —O—$R^5$, wherein $R^5$ is selected from hydrogen and —$(C_1–C_4)$-alkyl,
   —$N(R^5)$—$R^6$, wherein $R^5$ and $R^6$ are each selected independently from hydrogen and —$(C_1–C_4)$-alkyl,
   halogen, or
   a keto radical,
   —$C(O)$—$OR^5$, wherein $R^5$ is hydrogen or —$(C_1–C_4)$-alkyl, or
   —$C(O)$—$N(R^7)$—$R^8$, wherein $R^7$ and $R^8$ are each selected independently from hydrogen, —$(C_1–C_4)$-alkyl-OH, —O—$(C_1–C_4)$-alkyl and —$(C_1–C_4)$-alkyl;
R3 is hydrogen or —$(C_1–C_4)$-alkyl;
R4 is a heteroaryl radical, which is selected from pyrrole, furan, thiophene, imidazole, pyrazole, oxazole, isoxazole, thiazole, isothiazole, tetrazole, 1,2,3,5-oxathiadiazole-2-oxides, triazolones, oxadiazolone, isoxazolone, oxadiazolidinedione, triazole, 3-hydroxypyrro-2,4-diones, 5-oxo-1,2,4-thiadiazoles, pyridine, pyrazine, pyrimidine, indole, isoindole, indazole, phthalazine, quinoline, isoquinoline, quinoxaline, quinazoline, cinnoline, β-carboline and benzofused cyclopenta derivatives or cyclohexa derivatives of the heteroaryl radical, wherein the heteroaryl radical is optionally substituted one, two or three times by —$(C_1–C_5)$-alkyl, —$(C_1–C_5)$-alkoxy, halogen, nitro, amino, trifluoromethyl, hydroxyl, hydroxy-$(C_1–C_4)$-alkyl, methylenedioxy, ethylenedioxy, formyl, acetyl, cyano, hydroxycarbonyl, aminocarbonyl or —$(C_1–C_4)$-alkoxycarbonyl, or an aryl radical which is selected from phenyl, naphthyl, 1-naphthyl, 2-naphthyl, biphenylyl, 2-biphenylyl, 3-biphenylyl and 4-biphenylyl, anthryl and fluorenyl, wherein the aryl radical is optionally substituted one, two, or three times by $C_1–C_5$-alkyl, —$(C_1–C_5)$-alkoxy, halogen, nitro, amino, trifluoromethyl, hydroxyl, hydroxy-$(C_1–C_4)$-alkyl, methylenedioxy, ethylenedioxy, formyl, acetyl, cyano, hydroxycarbonyl, aminocarbonyl or —$(C_1–C_4)$-alkoxycarbonyl; and
R11 is hydrogen,
   halogen chosen from F, Cl, I and Br,
   —$(C_1–C_4)$-alkyl,
   —CN,
   —$CF_3$, —OR⁵, wherein R⁵ is hydrogen or —(C₁–C₄)-alkyl,
—N(R⁵)—R⁶, wherein R⁵ and R⁶ are selected independently from hydrogen and —(C₁–C₄)-alkyl,
—C(O)—R⁵, wherein R⁵ is hydrogen or —(C₁–C₄)-alkyl, or
—S(O)ₓ—R⁵, wherein x is the integer zero, 1 or 2, and wherein R⁵ is hydrogen or —(C₁–C₄)-alkyl, or a stereoisomer or a mixture of stereoisomers in any ratio of the compound, or a pharmaceutically acceptable salt of the compound.

2. The compound according to claim 1, wherein
X is N or CH;
M is N or CH;
R1 is hydrogen,
halogen chosen from F, Cl, I and Br,
—(C₁–C₄)-alkyl,
—CN,
—CF₃,
—OR⁵, wherein R⁵ is hydrogen or —(C₁–C₄)-alkyl,
—N(R⁵)—R⁶, wherein R⁵ and R⁶ are selected independently from hydrogen and —(C₁–C₄)-alkyl,
—C(O)—R⁵, wherein R⁵ is hydrogen or —(C₁–C₄)-alkyl, or
—S(O)ₓ—R⁵, wherein x is the integer zero, 1 or 2, and wherein R⁵ is hydrogen or —(C₁–C₄)-alkyl;
R2 is a heteroaryl radical, which is selected from imidazole, isothiazole, isoxazole, 2-isoxazolidine, isoxazolidine, isoxazolone, 1,3,4-oxadiazole, oxadiazolidinedione, 1,2,3,5-oxadiazolone, oxazole, 5-oxo-4,5-dihydro [1,3,4]oxadiazole, tetrazole, thiadiazole, thiazole, triazole and triazolone, wherein the heteroaryl radical is optionally substituted one, two, or three times by a keto radical, F, Cl, I, Br, or —(C₁–C₂)-alkyl, or —C(O)—N(R⁷)—R⁸, wherein R⁷ and R⁸ are each selected independently from hydrogen, —(C₁–C₄)-alkyl-OH, —O—(C₁–C₄)-alkyl and —(C₁–C₄-alkyl);
R3 is hydrogen, methyl or ethyl;
R4 is a heteroaryl radical which is selected from pyridine, pyrazine, pyrimidine, pyrrole, furan, thiophene, imidazole, pyrazole, oxazole, isoxazole, thiazole, triazole and isothiazole, wherein the heteroaryl radical is optionally substituted one, two or three times by —(C₁–C₄)-alkyl, —(C₁–C₄)-alkoxy, F, Cl, I, Br, nitro, amino, trifluoromethyl, hydroxyl, hydroxy-(C₁–C₄)-alkyl, methylenedioxy, ethylenedioxy, formyl, acetyl, cyano, hydroxycarbonyl, aminocarbonyl or —(C₁–C₄)-alkoxycarbonyl, or phenyl, wherein the phenyl is optionally substituted one, two or three times by F, Cl, I, Br, CF₃, —OH, —(C₁–C₄)-alkyl or —(C₁–C₄)-alkoxy; and
R11 is hydrogen,
halogen chosen from F, Cl, I and Br,
—(C₁–C₄)-alkyl,
—CN,
—CF₃,
—OR⁵, wherein R⁵ is hydrogen or —(C₁–C₄)-alkyl,
—N(R⁵)—R⁶, wherein R⁵ and R⁶ are selected independently from hydrogen and —(C₁–C₄)-alkyl,
—C(O)—R⁵, wherein R⁵ is hydrogen or —(C₁–C₄)-alkyl, or
—S(O)ₓ—R⁵, wherein x is the integer zero, 1 or 2, and wherein R⁵ is hydrogen or —(C₁–C₄)-alkyl.

3. The compound according to claim 1, including its designated sterochemical center, which is:

N-[(S)-2-diphenylamino-1-(5-oxo-4,5-dihydro[1,3,4] oxadizol-2-yl)ethyl]-2-(2-methylaminopyrimidin-4-yl)-1H-indole-5-carboxamide,
N-[(S)-1-(5-oxo-4,5-dihydro-1,3,4-oxadiazol-2-yl)-2-(phenylpyridin-2-ylamino)ethyl]2- (2-methylaminopyrimidin-4-yl)-1H-indole-5-carboxamide,
N-[1-carbamoyl-2-(phenylthiazol-2-ylamino)ethyl]-(S)-2-(2-methylaminopyrimidin-4-yl)-1H-indol-5-carboxamide,
N-[1-methoxycarbamoyl-2-(phenylpyridin-2-ylamino) ethyl]-(S)-2-(2-methylaminopyrimidin- 4-yl)-1H-indole-5-carboxamide,
(S)-2-{]2-(2-methylaminopyrimidin-4-yl)-1H-indole-5-carbonyl]amino}-3-[phenyl- (4-trifluoromethylpyrimidin-2-yl)amino]propionic acid, or
N-((S)-1-carbamoyl-2-diphenylaminoethyl)-2-(2-methylaminopyrimidin-4-yl)-1H- benzimidazole-5-carboxamide, or or a pharmaceutically acceptable salt of the compound.

4. The compound according to claim 1, including its designated sterochemical center, which is:

N-{1-carbamoyl-2-[(4-fluorophenyl)pyridin-2-ylamino] ethyl}-2-(2- methylaminopyrimidin-4-yl)-1H-indole-5-carboxamide,
N-{1-carbamoyl-2-[(4-fluorophenyl)pyridin-2-ylamino] ethyl}-2-(2-aminopyrimidin-4-yl)-1H- indole-5-carboxamide,
N-[2-[(4-fluorophenyl)pyridin-2-ylamino]-1-(4H-[1,2,4] triazol-3-yl)ethyl}-2- (2-methylaminopyrimidin-4-yl)-1H-indole-5-carboxamide,
N-{1-carbamoyl-2-[(phenyl)pyridin-2-ylamino]ethyl}-2-(2-aminopyrimidin-4-yl)-1H-indole- 5-carboxamide,
N-{1-carbamoyl-2-[(phenyl)pyridin-2-ylamino] ethyl}-2-(2-methylaminopyrimidin-4-yl)-1H- indole-5-carboxamide,
N-[1-(2-hydroxyethylcarbamoyl)-2-(phenylpyrimidin-2-ylamino)ethyl]- 2-(2-methylaminopyrimidin-4-yl)-1H-indole-5-carboxamide,
N-{1-carbamoyl-2-[(4-fluorophenyl)-(5-methylpyrimidin-2-yl)amino]ethyl}- 2-(2-methylaminopyrimidin-4-yl)-1H-indole-5-carboxamide,
N-{1-carbamoyl-2-[(phenyl)pyrimidin-2-ylamino] ethyl}-2-(2-methylaminopyrimidin-4-yl)-1H- benzimidazole-5-carboxamide, or
N-{1-carbamoyl-2-[(phenyl)pyridin-2-ylamino]ethyl}-2-(2-methylaminopyrimidin-4-yl)-1H- benzimidazole-5-carboxamide, or a pharmaceutically acceptable salt of the compound.

5. A process for preparing a compound according to claim 1, comprising,
a) reacting a compound of formula IV,

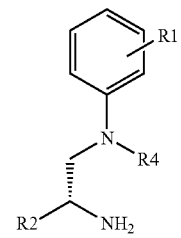

(IV)

wherein R1, R2 and R4 are as defined above,
with an acid chloride or an activated ester of the compound of the formula III,

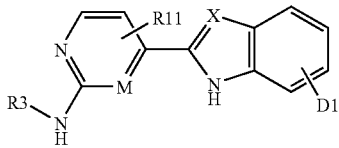

wherein D1 is —COOH and R11, X, M and R3 are as defined above, in the presence of a base, or where appropriate, in the presence of a dehydrating agent in solution, and converting the product into a compound of the formula I, b) separating the compound of the formula I, which has been prepared by method a) and which, on account of its chemical structure, appears in enantiomeric forms, into the pure enantiomers by means of forming salts with enantiomerically pure acids or bases, chromatography on chiral stationary phases or derivatization using chiral enantiomerically pure amino acids, separating the resulting diastereomers and eliminating the chiral auxiliary groups, and c) isolating the compound of the formula I which has been prepared by methods a) or b) in free form, or d) converting it into pharmaceutically acceptable salts when acidic or basic groups are present.

6. A pharmaceutical composition comprising a pharmaceutically effective amount of the compound according to claim 1 and a pharmaceutically acceptable carrier.

* * * * *